United States Patent
Yang et al.

(10) Patent No.: US 8,653,131 B2
(45) Date of Patent: Feb. 18, 2014

(54) POLYMERIC BENZYL CARBONATE-DERIVATIVES

(75) Inventors: Guohan Yang, Mansfield, MA (US); Ton That Hai, Round Lake, IL (US); Bennett P. Melnick, Chicago, IL (US); Paul Sanders, Greendale, WI (US); Cong Jiang, Gurnee, IL (US); Catherine Quinn, Mundelein, IL (US); Jie Li, Cary, NC (US); Arounaguiry Ambroise, Cary, NC (US); Larry R. Brown, Newton, MA (US)

(73) Assignees: Baxter Healthcare S.A., Glattpark (Opfikon) (CH); Baxter International Inc., Deefield, IL (US)

( * ) Notice: Subject to any disclaimer, the term of this patent is extended or adjusted under 35 U.S.C. 154(b) by 276 days.

(21) Appl. No.: 12/545,406

(22) Filed: Aug. 21, 2009

(65) Prior Publication Data

US 2010/0048483 A1    Feb. 25, 2010

Related U.S. Application Data

(60) Provisional application No. 61/189,751, filed on Aug. 22, 2008.

(51) Int. Cl.
| | |
|---|---|
| C07D 207/46 | (2006.01) |
| C07C 271/08 | (2006.01) |
| C07C 69/63 | (2006.01) |
| C07C 69/66 | (2006.01) |
| A61K 31/27 | (2006.01) |

(52) U.S. Cl.
USPC ........... 514/489; 514/478; 514/484; 548/547; 560/145; 560/226; 560/186

(58) Field of Classification Search
USPC ........... 514/478, 484, 489; 548/547; 560/145, 560/226, 186
See application file for complete search history.

(56) References Cited

U.S. PATENT DOCUMENTS

| | | | |
|---|---|---|---|
| 3,960,871 A | 6/1976 | Harris et al. | |
| 3,972,880 A | 8/1976 | Harris et al. | |
| 3,991,194 A | 11/1976 | Harris et al. | |
| 4,025,630 A | 5/1977 | Dren et al. | |
| 4,042,694 A | 8/1977 | Harris et al. | |
| 4,046,889 A | 9/1977 | Ondetti et al. | |
| 4,081,449 A | 3/1978 | Winn | |
| 4,105,776 A | 8/1978 | Ondetti et al. | |
| 4,154,840 A | 5/1979 | Ondetti et al. | |
| 4,244,957 A | 1/1981 | Ramuz | |
| 4,355,033 A | 10/1982 | Ramuz | |
| 4,439,364 A * | 3/1984 | Johnson | 540/529 |
| 4,511,720 A | 4/1985 | Ramuz | |
| 4,786,646 A | 11/1988 | Guthrie et al. | |
| 4,788,206 A | 11/1988 | Guthrie et al. | |
| 4,812,573 A | 3/1989 | Durant et al. | |
| 4,916,145 A | 4/1990 | Tilley et al. | |
| 4,927,826 A | 5/1990 | Guthrie et al. | |
| 4,927,838 A | 5/1990 | Guthrie et al. | |
| 4,970,210 A | 11/1990 | Brooks et al. | |
| 4,975,438 A | 12/1990 | Guthrie et al. | |
| 4,981,873 A | 1/1991 | Witte et al. | |
| 5,053,338 A | 10/1991 | Bray et al. | |
| 5,086,052 A | 2/1992 | Brooks et al. | |
| 5,096,904 A | 3/1992 | Wheeler et al. | |
| 5,204,463 A | 4/1993 | Wheeler et al. | |
| 5,491,145 A | 2/1996 | Miyake et al. | |
| 6,255,494 B1 | 7/2001 | Britton et al. | |
| 6,284,756 B1 | 9/2001 | Chirgadze et al. | |
| 6,350,774 B1 | 2/2002 | Bach et al. | |
| 6,413,507 B1 | 7/2002 | Bentley et al. | |
| 6,515,100 B2 | 2/2003 | Harris | |
| 6,703,422 B2 | 3/2004 | Dasseux et al. | |
| 6,713,471 B1 | 3/2004 | Robichaud et al. | |
| 6,899,867 B2 | 5/2005 | Bentley et al. | |
| 6,902,850 B2 | 6/2005 | Wariishi et al. | |
| 6,992,168 B2 | 1/2006 | Bentley et al. | |
| 7,205,380 B2 | 4/2007 | Bentley et al. | |
| 7,211,672 B2 | 5/2007 | Ghosh et al. | |
| 7,504,508 B2 | 3/2009 | Ghosh et al. | |
| 2002/0007071 A1 | 1/2002 | Britton et al. | |
| 2004/0176270 A1 | 9/2004 | Chen et al. | |
| 2004/0192743 A1 | 9/2004 | Mjalli et al. | |
| 2004/0192769 A1 * | 9/2004 | Greenwald et al. | 514/483 |
| 2005/0014812 A1 | 1/2005 | Hayashida et al. | |
| 2005/0020694 A1 | 1/2005 | Dasseux et al. | |

(Continued)

FOREIGN PATENT DOCUMENTS

| | | |
|---|---|---|
| CA | 1102337 | 6/1981 |
| CA | 1103255 | 6/1981 |

(Continued)

OTHER PUBLICATIONS

Greenwald et al. J. Med. Chem. 1999, 42, 3657-3667.*
International Search Report for PCT/US2009/054595 date of mailing Jul. 2, 2010.
Written Opinion for PCT/US2009/054595 date of mailing Jul. 2, 2010.
U.S. Appl. No. 12/398,894, filed Mar. 5, 2009, Beduneau et al.
U.S. Appl. No. 12/467,230, filed May 15, 2009, Rabinow et al.
Afzal et al., "Syntheses of perfluoroalkyl N-polyethoxylated amides", *J. Fluorine Chem.*, 34:385-93 (1987).
Andrews et al., "Reactions of transition-metal atoms with arenes, arene-functionalized alkanes, oligo(ethylene oxides), and polysiloxanes", *Inorg. Chem.*, 25:2587-95 (1986).

(Continued)

Primary Examiner — Joseph Kosack
Assistant Examiner — Matthew Coughlin
(74) Attorney, Agent, or Firm — Marshall, Gerstein & Borun LLP

(57) ABSTRACT

The present invention relates to polymeric derivatives, which can be conjugated to an amino-containing drug to improve its in vivo properties. The polymeric derivative can subsequently be released to yield the drug in its native form. Methods of preparing and using these polymeric derivatives and drug conjugates are described.

44 Claims, No Drawings

(56) References Cited

U.S. PATENT DOCUMENTS

| | | | |
|---|---|---|---|
| 2005/0101572 A1 | 5/2005 | Goel | |
| 2006/0029586 A1 | 2/2006 | Chen et al. | |
| 2006/0069237 A1 | 3/2006 | Bentley et al. | |
| 2006/0079696 A1 | 4/2006 | Masson et al. | |
| 2006/0106061 A1 | 5/2006 | Ghosh et al. | |
| 2009/0181966 A1 | 7/2009 | Ghosh et al. | |

FOREIGN PATENT DOCUMENTS

| | | |
|---|---|---|
| CA | 1103256 | 6/1981 |
| CA | 1103257 | 6/1981 |
| DE | 2703828 | 8/1977 |
| DE | 3734751 | 5/1989 |
| DE | 3925256 | 1/1991 |
| EP | 298466 | 1/1989 |
| GB | 1584421 | 2/1981 |
| JP | 57192323 | 11/1982 |
| JP | 4211099 | 8/1992 |
| JP | 5222187 | 8/1993 |
| JP | 7309898 | 11/1995 |
| JP | 9118699 | 5/1997 |
| JP | 2006327984 | 12/2006 |
| JP | 2007277429 | 10/2007 |
| WO | WO-90/09986 | 9/1990 |
| WO | WO-97/25041 | 7/1997 |
| WO | WO-98/48798 | 11/1998 |
| WO | WO-98/49161 | 11/1998 |
| WO | WO-02/30884 | 4/2002 |
| WO | WO-2004/008101 | 1/2004 |
| WO | WO-2004/063250 | 7/2004 |
| WO | WO-2004/071447 | 8/2004 |
| WO | WO-2004/089280 | 10/2004 |
| WO | WO-2005/068418 | 7/2005 |
| WO | WO-2005/095395 | 10/2005 |
| WO | WO-2005/100321 | 10/2005 |
| WO | WO 2006/076471 | 7/2006 |
| WO | WO 2006076471 A2 * | 7/2006 |
| WO | WO-2006/099794 | 9/2006 |
| WO | WO-2006/104883 | 10/2006 |
| WO | WO-2006/104884 | 10/2006 |
| WO | WO-2006/138572 | 12/2006 |
| WO | WO-2007/098826 | 9/2007 |
| WO | WO 2008/082669 | 7/2008 |
| WO | WO-2008/087529 | 7/2008 |
| WO | WO-2008/128951 | 10/2008 |
| WO | WO-2009/011285 | 1/2009 |

OTHER PUBLICATIONS

Baas et al., "Vitamin A analogs. IV. Attempted synthesis of 2,4,4-trimethyltetrahydrothiopyr-3-one", *Tetrahedron*, 22:285-91(1966).

Badjic et al., "The exclusivity of multivalency in dynamic covalent processes", *Angew. Chem. Int. Ed. Engl.*, 43:3273-8 (2004).

Bagirov et al., "Primary analysis of EEG in schoolchildren", *Doklady / Akademiia nauk Azerbaidzhanskoi SSR*, 39:67-70 (1983). [English abstract].

Ban, "Solid-liquid phase transfer catalytic synthesis of diethylene glycol monododecyl ether", *Huaxue Shiji*, 22:245-6 (2000).

Barth et al., "Synthesis of 6-O-Benzyl Guanine and its Conjugations with Linkers", *Zeitschrift fur Naturforschung, B: Chemical Sciences*, 59:802-6 (2004).

Bellasio et al., "2-Alkyl-3-bromopropionic acids", *Edizione Scientifica*, 24:719-24 (1969) (Italian Only).

Belohradsky et al., "Synthesis of homochiral acyclic mono- and bis($\alpha$-amino acid)s with oligo(oxyethylene) chains", *Collection of Czechoslovak Chemical Comm.*, 68:1319-25 (2003).

Bouzide et al., "Highly selective silver(I) oxide mediated monoprotection of symmetrical diols", *Tetrahedron Lett.*, 38:5945-8 (1997).

Bowman et al., "Amides as precursors of imidoyl radicals in cyclization reactions", *Tetrahedron*, 63:191-203 (2007).

Chen et al., "Efficient synthesis of polyethylene glycol monocarboxylate via Michael conjugate addition", *Synthetic Comm.*, 34:2425-32 (2004).

Chuchuryukin et al., "General Approach for Template-Directed Synthesis of Macroheterocycles by Ring-Closing Metathesis (RCM)", *Advanced Synthesis & Catalysis*, 347:447-62 (2005).

Collins et al., "Preparation of 2-(3-bromo-1-methylpropyl)-1,3-dioxolane and the corresponding chloride from 2-methylbutyrolactone", *Australian. J. Chem.*, 42:223-8 (1989).

Conze et al., "Characterization of PEGylated lysozyme by size exclusion and ion exchange chromatography", pp. 48-49 From: *The Applications Book*, Tosoh Bioscience (2008).

Diot et al., "Multivalent iminosugars to modulate affinity and selectivity for glycosidases", *Org. Biomol. Chem.*, 7:357-63 (2009).

Dobler et al., "Chirale poly(9,9'-spirobifluoren)-kronenether", *Angewandte Chemie*, 97:793-4 (1985).

Fernandes et al., "Polysialylated asparaginase: preparation, activity and pharmacokinetics" *Biochim Biophys Acta.*, 1341:26-34 (1997).

Francke et al., "Identification and synthesis of dimethylalkanes as sex attractants of female leaf miner moths (Lyonedtiidae)", *J. Biosciences*, 43:787-9 (1988).

Franke et al., "Synthesis of cannabinoid model compounds. Part 2. (3R,4R)-$\Delta$1 (6)-tetrahydrocannabinol-5''-oic acid and 4''(R,S)-methyl-(3R,4R)-$\Delta$1(6)-tetrahydrocannabinol-5''-oic acid", *Helvetica Chimica Acta*, 63:2508-14 (1980).

Ghosh et al., "N,N'-dissuccinimidyl carbonate: a useful reagent for alkoxycarbonylation of amines", *Tetrahedron Lett.*, 33:2781-4 (1992).

Goyal et al., "Role of benzyl alcohol in the prevention of heat-induced aggregation and inactivation of hen egg white lysozyme", *Eur. J. Pharmaceutics and Biopharmaceutics*, 71:367-76 (2009).

Greenwald et al., "Effective drug delivery by PEGylated drug conjugates", *Adv. Drug Deliv. Rev.*, 55:217-50 (2003).

Greenwald et al., "Controlled release of proteins from their poly(ethylene glycol) conjugates: drug delivery systems employing 1,6-elimination", *Bioconjug. Chem.*, 14:395-403 (2003).

Greenwald et al., "Drug delivery systems employing 1,4- or 1,6-elimination: poly(ethylene glycol) prodrugs of amine-containing compounds", *J. Med. Chem.*, 42:3657-67 (1999).

Greenwald et al., "PEG thiazolidine-2-thione, a novel reagent for facile protein modification: conjugation of bovine hemoglobin", *Bioconjugate Chem.*, 7:638-41 (1996).

Guidry et al., "Bifunctional [c2]daisy-chains and their incorporation into mechanically interlocked polymers", *J. Am. Chem. Soc.*, 129:8944-5 (2007).

Hiremath et al., "Convenient one-pot synthesis of (Z)-4-Benzyloxy-2-buten-1-ol", *Indian J. Chem., Section B: Organic Chemistry Including Medicinal Chemistry*, 27B:558 (1988).

Ho et al., "Alkylglycidic Acids: Potential New Hypoglycemic Agents", *J. Med. Chem.*, 29:2184-90 (1986).

Houghton et al., "$\omega$-Hydroxy and ($\omega$-amino carboxylic acid derivatives for the preparation of ester and amide crown ethers", *Synthetic Comm.*, 19:3199-209 (1989).

Houseman et al., "Efficient solid-phase synthesis of peptide-substituted alkanethiols for the preparation of substrates that support the adhesion of cells", *J. Org. Chem.*, 63:7552-5 (1998).

Ibarzo et al., "1,2-Dibromoethane in the synthesis of 2-bromo esters: bromination versus alkylation", *Tetrahedron*, 50:9825-30 (1994).

Inokuma et al., "Synthesis of crownophanes possessing three pyridine rings", *Tetrahedron*, 63:5088-94 (2007).

Jones et al., "Synthesis of 9-azasteroids. II. Synthesis of $\beta$-cyano- and $\beta$-carbethoxy-3-and 4-oxo-1,2,3,4,5,6-hexahydrobanzo(c)quinolizines", *Tetrahedron*, 21:2961-71 (1965).

Jungk et al., "Preparation of monoallyl ethylene glycols", *Organic Preparations and Procedures International*, 15:152-3 (1983).

Kenda et al., "Discovery of 4-substituted pyrrolidone butanamides as new agents with significant antiepileptic activity", *J. Med. Chem.*, 47:530-49 (2004).

Komiotis et al., "Preparation of monotritylated symmetric 1,n-diols", *Synthetic Comm.*, 23:531-4 (1993).

Krippner et al., "Synthesis and antiviral activity of dimeric capsid-binding inhibitors of human rhinovirus (HRV)", *Australian J. Chem.*, 57:553-64 (2004).

Lahiri et al., "Biospecific binding of carbonic anhydrase to mixed SAMs presenting benzenesulfonamide ligands: A model system for studying lateral steric effects", *Langmuir*, 15:7186-98 (1999).

(56) References Cited

OTHER PUBLICATIONS

Lemarchand et al., "Synthesis of Chiral ansa-Bridged Macrocyclic Lactams ([16]Metacyclophanes) Related to Geldanamycin", *Synthesis*, 12:1377-90 (2005).
Lee et al., "Drug delivery systems employing 1,6-elimination: releasable poly(ethylene glycol) conjugates of proteins", *Bioconjug. Chem.*, 12:163-9 (2001).
Levandovskaya, "Synthesis of polyhydroxyethylene glycols with an acenaphthene ring", *Journal of Organic Chemistry of the USSR*, 25:332-6 (1989).
Li et al., "Studies on carbohydrates XXXII—chemoselective synthesis of mannosamine glycosides through nonregio-selective azidonitration of lactal", *Carbohydrate Letters*, 3:349-54 (1999).
Li et al., "Syntheses of novel tripodal calix[n]cryptands (n = 4, 6) and their extraction abilities toward cations", *Eur. J. Org. Chem.*, 2000:485-90 (2000).
Li et al., "Synthesis and characterization of pentaerythritol-derived oligoglycol and their application to catalytic Wittig-type reactions", *J. Org. Chem.*, 69:3986-9 (2004).
Li et al., "Synthesis of novel heterobifunctional isocyanato cross-linkers and their applications for the preparation of 10-hydroxycamptothecin and SN-38 conjugates with melanotransferrin P97", *Synthetic Comm.*, 37:1899-915 (2007).
Michalovic et al., "Aqueous solution behavior of oxyethylene-substituted poly(acrylic acid)s", *Polymer Preprints*, 39:335-6 (1998).
Nabeshima et al., "Cooperative control of ion and molecular recognition by molecular assembling", *J. Org. Chem.*, 63:3802-3 (1998).
Newkome et al., "Chemistry of heterocyclic compounds. 23. Synthesis of multiheteromacrocycles possessing 2,6-pyridino subunits connected by carbon-oxygen linkages", *J. Org. Chem.*, 42:1500-8 (1977).
Newkome et al., "Chemistry of heterocyclic compounds. 98. Syntheses, conformational studies, and reactions of heteromacrocycles. Bis(2-pyridyl) ketone derivatives", *J. Org. Chem.*, 49:2961-71 (1984).
Newkome et al., "Polydentate ketal coronands containing 2,6-pyridino and/or 6,6'-(2,2'-bipyridino) subunits: synthesis, characterization, structural aspects, and conformational changes upon complexation", *J. Org. Chem.*, 51:970-4 (1986).
Nicolaus et al., "Substances acting on the central nervous system. XXV. Reactions of the α-substituted β-lactones. 2. A new general synthesis for α-substituted propionic acid and its derivatives", *J. Org. Chem.*, 26:1076-84 (1961).
Pale-Grosdemange et al., "Formation of self-assembled monolayers by chemisorption of derivatives of oligo(ethylene glycol) of structure HS(CH2)11(OCH2CH2)mOH on gold", *J. Am. Chem. Soc.*, 113:12-20 (1991).
Pasut et al., "PEG conjugates in clinical development or use as anticancer agents: An overview", *Adv. Drug Delivery Rev.*, 61:1177-88 (2009).
Pasut et al., "Polymer-drug conjugation, recent achievements and general strategies", *Progress in Polymer Sci.*, 32:933-61 (2007).
Pasut et al., "New active poly(ethylene glycol) derivative for amino coupling", *React. Func. Polymers*, 67:529-39 (2007).
Peleg-Shulman et al., "Reversible PEGylation: a novel technology to release native interferon alpha2 over a prolonged time period", *J. Med. Chem.*, 47:4897-904 (2004).
Perrey et al., "An improved method for cysteine alkylation", *Tetrahedron Lett.*, 42:1859-61 (2001).
Porter-Peden et al., "Estimating kinetic and thermodynamic parameters from single molecule enzyme-inhibitor interactions", *Langmuir*, 24:11556-61 (2008).
Qing et al., "Synthesis and properties of monoalkyl ethers of diethylene glycol", *Shangqiu Shifan Xueyan Xuebao*, 16:67-9 (2000).
Razdan et al., "Drugs derived from cannabinoids. 2. Basic esters of nitrogen and carbocyclic analogs", *J. Med. Chem.*, 19:454-61 (1976).
Reder et al., "Novel alkaloids from the poison glands of ants Leptothoracini", *Helvetica Chimica Acta*, 78:73-9 (1995).
*Remington's Pharmaceutical Sciences*, 18th ed., Easton, Penn: Mack Publishing Co. pp. 1435-712 (1990).
Roberts et al., "Chemistry for peptide and protein PEGylation", *Adv. Drug Deliv. Rev.*, 54:459-76 (2002).
Roberts et al., "Attachment of degradable poly(ethylene glycol) to proteins has the potential to increase therapeutic efficacy", *J. Pharm. Sci.*, 87:1440-5 (1998).
Schmidt et al., "Synthesis of cannabinoid model compounds. Part 3. (6aR, 10aR)-N-ethylΔ8-tetrahydrocannabinol-18-amide, (6aR, 10aR, 17 RS)-N-ethyl-17-methyl-Δ8-tetrahydrocannabinol-18-amide and (6aR, 10aR)-17,18-didehydro-Δ8-tetrahydrocannabinol", *Helvetica Chimica Acta*. 66:2564-71 (1983).
SciFinder database results for Iodo-t-butyl structure search run on Nov. 18, 2009.
SciFinder database results for biiodo-t-butyl structure search run on Dec. 4, 2009.
SciFinder database results for triiodine-t-butyl structure search run on Dec. 4, 2009.
SciFinder database results for 4-iodine-t-butyl structure search run on Dec. 4, 2009.
SciFinder database results for bromo-t-butyl structure run on Nov. 18, 2009 and Dec. 4, 2009.
SciFinder database results for bibromo-t-butyl structure search run on Dec. 4, 2009.
SciFinder database results for tribromine-t-butyl structure search run on Dec. 4, 2009.
SciFinder database results for 4-bromine-t-butyl structure search run on Dec. 4, 2009.
SciFinder database results for chloro-t-butyl structure search run on Dec. 4, 2009.
SciFinder database results for bichlorine-t-butyl structure search run on Dec. 4, 2009.
SciFinder database results for trichlorine-t-butyl structure search run on Dec. 4, 2009.
SciFinder database results for 4-chloro-t-butyl structure search run on Dec. 4, 2009.
Shechter et al., "Reversible PEGylation of peptide YY3-36 prolongs its inhibition of food intake in mice", *FEBS Left.*, 579:2439-44 (2005).
Shuai et al., "Novel biodegradable ternary copolymers *hy*-PEI-*g*-PCL-*b*-PEG: synthesis, characterization, and potential as efficient nonviral gene delivery vectors", *Macromolecules*, 36:5751-9 (2003).
Snider et al., "Total synthesis of (±)-leporin A", *J. Org. Chem.*, 61:2839-44 (1996).
Stone et al., "Unusual benefits of macromolecular shielding by polyethylene glycol for reactions at the diffusional limit: the case of factor VIIai and tissue factor", *Biochemistry*, 41: 15820-5 (2002).
Sugiwara et al., "Synthesis of ω-(methoxycarbon)alkyl and 9-(methoxycarbonyl)-3,6-dioxanonyl glycopyranosides for the preparation of carbohydrate-protein conjugates", *Carbohydrate Res.*, 23:117-49 (1992).
Sugiyama et al., "An alternative synthesis of deuterated cytokinins", *Nucleic Acids Symposium Series*, 8:s27-s30 (1980).
Sugiyama et al., "An efficieent synthesis of deuterated (±)-dihydrozeatin-d5 and its riboside", *Agric. Biol. Chem.*, 44:2755-6 (1980).
Szurmai et al., "Diethylene and triethylene glycol spacers for the preparation of neoglycoproteins", *Acta Chimica Hungarica*, 126:259-69 (1989).
Terent'Ev et al., "Telomerization of ethylene with methyl bromoacetate", *Izvestiya Akademii Nauk SSSR, Seriya Khimicheskaya*, 8:1837-9 (1969) (Russian only).
Topiwala et al., "Studies of a novel biomimetic radical spirocyclization", *J. Chem. Soc.*, 7:1185-92 (1998).
Tsubery et al., "Prolonging the action of protein and peptide drugs by a novel approach of reversible polyethylene glycol modification", *J. Biol. Chem.*, 279:38118-24 (2004).
Van Der Leij et al., "A novel synthesis of 2'-hydroxy-1',3'-xylyl crown ethers", *Tetrahedron*, 37:3661-6 (1981).
Wang et al., "Study on glycosylated prodrugs of toxoflavins for antibody-directed enzyme tumor therapy", *Carbohydr. Res.*, 342:1254-60 (2007).

(56) References Cited

OTHER PUBLICATIONS

Watson et al., "An enantioselective synthesis of sulphonamide hydroxamic acids as matrix metalloproteinase inhibitors", *Tetrahedron Lett.*, 43:683-5 (2002).

Wei et al., "Synthesis and characterization of niclosamide derivatives", *Huaxue Tongbao*, 70:707-9 (2007).

Weitzhandler et al., "Protein variant separations by cation-exchange chromatography on tentacle-type polymeric stationary phases", *J. Chromatography A*, 828:365-72 (1998).

Wermuth et al., "Synthesis and structure-activity relationships of a series of aminopyridazine derivatives of .gamma.-aminobutyric acid acting as selective GABA-A antagonists", *J. Med. Chem.*, 30:239-49 (1987).

Westerlind et al., "Ligands of the asialoglycoprotein receptor for targeted gene delivery, part 1: Synthesis of and binding studies with biotinylated cluster glycosides containing N-acetylgalactosamine", *Glycoconj. J.*, 21:227-41 (2004).

Winn et al., "Drugs derived from cannabinoids. 5. Δ6a,10a,-tetrahydrocannabinol and heterocyclic analogs containing aromatic side chains", *J. Med. Chem.*, 19:461-71 (1976).

Wissner et al., "Analogs of platelet activating factor. 5. Multiple oxygen substitution of the alkoxy chain", *J. Med. Chem.*, 29:1315-9 (1986).

Wosnick et al., "Synthesis and application of poly(phenylene ethynylene)s for bioconjugation: a conjugated polymer-based fluorogenic probe for proteases", *J. Am. Chem. Soc.*, 127:3400-5 (2005).

Xu et al., "Characterizing the modification of surface proteins with poly(ethylene glycol) to interrupt platelet adhesion", *Biomaterials*, 27:3125-35 (2006).

Zhang et al., "Structural studies of Vγ2Vdelta2 T cell phosphoantigens", *Chem. Biol.*, 13:985-92 (2006).

Zhao et al., "A new platform for oligonucleotide delivery utilizing the PEG prodrug approach", *Bioconjugate Chem.*, 16:758-66 (2005).

Zhao et al., "Linear and branched bicin linkers for releasable PEGylation of macromolecules: controlled release in vivo and in vitro from mono- and multi-PEGylated proteins", *Bioconjug. Chem.*, 17:341-51 (2006).

Ziegler et al., "Synthesis of a highly functionalized carbon ring skeleton for the trichothecene anguidine", *J. Am. Chem. Soc.*, 112:2749-58 (1990).

* cited by examiner

POLYMERIC BENZYL CARBONATE-DERIVATIVES

CROSS-REFERENCE TO RELATED APPLICATIONS

This application claims the benefit of U.S. Provisional Application No. 61/189,751, filed Aug. 22, 2008, which is incorporated by reference in its entirety herein.

FIELD OF THE INVENTION

The present invention provides polymeric derivatives, which can be conjugated to an amino-containing drug to improve its in vivo properties. The polymeric derivatives can subsequently be released to yield the drug in its native form. Methods of preparing and using these polymeric derivatives and drug conjugates are described

BACKGROUND

The modification of drugs with poly(ethylene glycol) is a well-established process that improves their pharmacological and biological properties.

Protein and peptide drugs often have a short circulatory half-life in vivo, can have high immunogenicity, can undergo proteolytic degradation, and can have low solubility. Also, prolonged maintenance of therapeutically active drugs in the circulation is a desirable feature of obvious clinical importance.

An attractive strategy for improving the clinical properties of protein or peptide drugs is a modification of the drugs with hydrophilic polymers e.g., polyalkylene oxides (Roberts et al., *Adv. Drug Rev.* 54, 459-476 (2002)) or polysaccharides, like polysialic acid (Fernandes et al., *Biochim. Biophys. Acta*, 1341, 26-34 (1997)), dextrans, or hydroxyalkyl starch. Although the modification of protein and peptide drugs with poly(ethylene glycol) (PEG) improves the stability and solubility of the protein or peptide, it often leads to reduced activity. However, subsequent release of PEG moieties from a PEGylated protein or peptide in vivo restores the activity of the protein or peptide. Thus, derivatization of proteins and peptides with releasable PEGs may convert a protein to a controlled-release prodrug with an enhanced circulatory lifetime. These improved biological properties have been shown, for example, in the case of interferon α-2 (Peleg-Shulman et al., *J Med Chem.* 47, 4897-4904 (2004)), exendin-4 (Tsubery et al., *J Biol Chem.* 37, 38118-38124 (2004)) and interferon-β-1b (Zhao et al., Bio-conjugate Chem. 17, 341-351 (2006)).

Drug molecules different from proteins and peptides also benefit from PEGylation. PEGylation of drug molecules increases the apparent size of the molecule, thus reducing renal filtration and altering biodistribution. In addition, the PEGylation of hydrophobic ligands increases their solubility in vivo. Finally, derivatization of drug molecules different from proteins and peptides with releasable PEGs provides a method of converting the drug into a controlled-release prodrug.

Several releasable linkers comprising PEG moieties have been suggested. U.S. Pat. No. 6,515,100 describes PEG and related polymer derivatives having weak, hydrolytically unstable linkages to proteins or peptides. However, hydrolysis of the unstable linkage to release PEG from the protein or peptide fails to provide the protein or peptide in its native form. Instead, the protein or peptide comprises an additional short molecular fragment, or tag.

U.S. Pat. No. 7,205,380 describes PEG derivatives, having sterically hindered linkages, that couple with alcohol or thiol groups of proteins or peptides to result in ester or thioester bonds with decreased hydrolytic reactivity. This decreased hydrolytic activity results from the conjugation of alkyl or aryl groups to the carbon adjacent to the carbonyl carbon of the ester or thioester linkage. The patent also discloses that hydrolytic delivery of drugs from PEG esters can be controlled by controlling the number of linking methylene groups in a spacer between the terminal PEG oxygen and the carbonyl group of the attached carboxylic acid or carboxylic acid derivative. The PEG linker of the patent is not optimal with amino-containing proteins because the resulting amide would be more stable to hydrolysis and less able to release PEG from the protein.

U.S. Pat. Nos. 6,413,507 and 6,899,867 describe hydrolytically degradable carbamate derivatives of poly(ethylene glycol). The PEG moiety is conjugated to the protein through a nonhydrolyzable linker attached to an aryl group, which is linked to the protein through a carbamate.

International Publication Nos. WO 04/089280 and WO 06/138572 describe hydrolyzable fluorene-based PEG constructs.

Greenwald et al., (*J Med Chem.* 42, 3657-3667 (1999)) outlines a general methodology for synthesizing PEG prodrugs of amino-containing compounds. PEG conjugates are described, which follow a double prodrug strategy that relies, first, on enzymatic separation of PEG, followed by a rapid 1,4- or 1,6-benzyl elimination reaction, releasing the conjugated amino-containing drug bound in the form of a carbamate.

SUMMARY

The present invention provides polymeric derivatives, which can be conjugated to drugs to improve their in vivo properties, such as half-life, solubility, and/or circulation. The polymeric derivatives can subsequently be released to yield the drug in its native form. Without intending to be bound by any particular theory, the release of the polymeric derivative from the drug follows a multi-step release mechanism.

In one aspect, the present invention provides polymeric derivatives of the general Formula I:

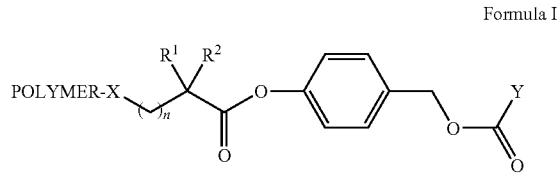

Formula I wherein Y is an activating group capable of being readily displaced by an amino group of a drug to form a carbamate linkage;

n is ≥1;

X is selected from the group consisting of O, S and NR³, wherein R³ is selected from the group consisting of hydrogen, ($C_1$-$C_6$)-alkyl, ($C_1$-$C_6$)-alkylenearyl, and aryl;

POLYMER is a water soluble, non-peptidic polymer; and

R¹ and R² are independently selected from the group consisting of hydrogen, ($C_1$-$C_6$)-alkyl, ($C_1$-$C_6$)-alkylenearyl, and aryl.

In another aspect, the present invention provides drug conjugates or salts, esters, or solvates thereof of Formula II:

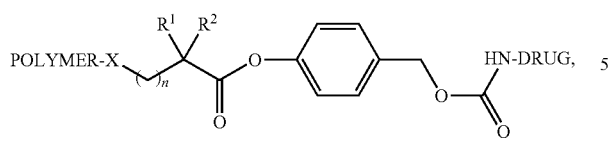

Formula II wherein X is selected from the group consisting of O, S and NR³; n is ≥1; POLYMER is a water soluble, non-peptidic polymer; R¹ and R² are independently selected from the group consisting of hydrogen, $(C_1$-$C_6)$-alkyl, $(C_1$-$C_6)$-alkylenearyl, and aryl; R³ is selected from the group consisting of hydrogen, $(C_1$-$C_6)$-alkyl, $(C_1$-$C_6)$-alkylenearyl, and aryl; and DRUG is an amino-containing molecule, peptide, or protein. The drug can be a plasma protein or a blood coagulation factor. In specific embodiments, the drug can be erythropoietin, Factor H, Factor VIII, von Willebrand Factor, Factor VIIa, or Factor IX.

In still another aspect, the present invention provides pharmaceutical formulations of the drug conjugates disclosed herein and a pharmaceutically acceptable excipient. In some embodiments, the formulation comprises drug conjugates encapsulated in a microparticle.

In yet another aspect, the present invention provides methods of treating a disease in a patient comprising administering to the patient a pharmaceutical formulation as disclosed herein. In some cases, the disease is a blood clotting disease and the drug of the drug conjugate is a plasma protein or blood coagulation factor.

In another aspect, the present invention provides compounds of structure A:

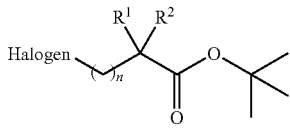

A wherein n is 1, 2, 3, or 4;

R¹ and R² are independently selected from the group consisting of hydrogen, $(C_1$-$C_6)$-alkyl, $(C_1$-$C_6)$-alkylenearyl, and aryl; and Halogen is Br, Cl, or I;

with the proviso that at least one of R¹ and R² is different from hydrogen.

In specific embodiments, the compound of structure A is selected from the group consisting of:

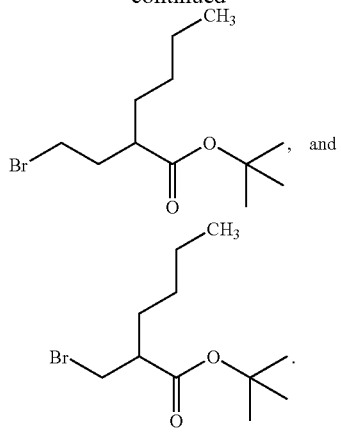

In another aspect, the present invention provides compounds of structure B:

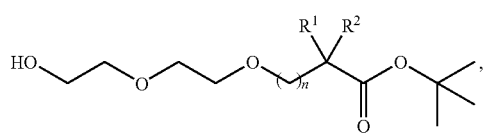

B wherein n is 1, 2, 3, or 4; and

R¹ and R² are independently selected from the group consisting of hydrogen, $(C_1$-$C_6)$-alkyl, $(C_1$-$C_6)$-alkylenearyl, and aryl;

with the proviso that at least one of R¹ and R² is different from hydrogen.

In specific embodiments, the compound of structure B is selected from the group consisting of:

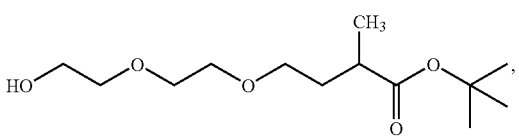

In another aspect, the present invention provides compounds of structure C:

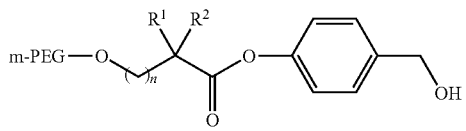

wherein n is 1, 2, 3, or 4;

$R^1$ and $R^2$ are independently selected from the group consisting of hydrogen, ($C_1$-$C_6$)-alkyl, ($C_1$-$C_6$)-alkylenearyl, and aryl; and m-PEG- is monomethoxy poly(ethylene glycol) having a molecular weight of about 200 to about 500,000;

with the proviso that at least one of $R^1$ and $R^2$ is different from hydrogen.

In specific embodiments, the compound of structure C is selected from the group consisting of:

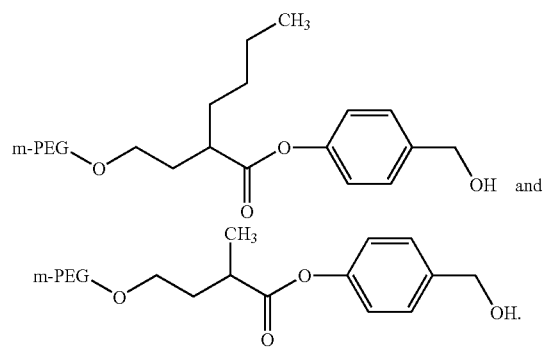

In another aspect, the present invention provides methods of preparing a compound of formula F, comprising mixing a compound of formula A, diethylene glycol, and a base to form a compound of formula B, which is then reacted with a base and monomethoxy poly(ethylene glycol) sulfonate ester, such as mPEG mesylate (mPEG-OMs) or fluorophenylsulfonate (mPEG-OTs(F)), to form the compound of formula F, as shown below:

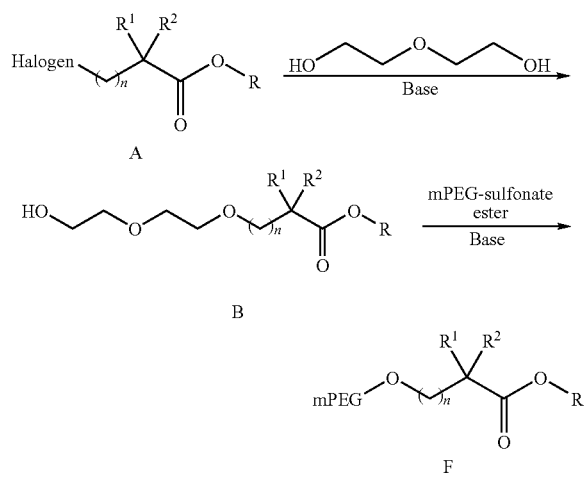

wherein n is 1, 2, 3, or 4; $R^1$ and $R^2$ are independently selected from the group consisting of hydrogen, ($C_1$-$C_6$)-alkyl, ($C_1$-$C_6$)-alkylenearyl, and aryl; and R is ($C_1$-$C_6$)-alkyl.

In another aspect, the present invention further provides drug conjugates having the general Formula II.

Formula II wherein POLYMER, X, $R^1$, $R^2$, and n are defined as in Formula I. DRUG is an amino-containing molecule, peptide, or protein capable of triggering a biological response, or is a molecule, peptide, or protein capable of triggering a biological response that is modified to comprise an amino group.

In another aspect, the present invention provides methods of manipulating the rate of release of the polymeric derivative from the drug.

DETAILED DESCRIPTION

The present invention provides polymeric derivatives, which can be conjugated to amino-containing drugs to improve their in vivo properties such as their half-lives, solubility, and/or in vivo circulation. The polymeric derivatives can subsequently be released from the drugs in vivo to yield the drug in its native form. It is theorized that the release of the polymeric derivative from the drug follows a multi-step release mechanism.

The instant invention describes the conjugation of a releasable polymeric derivative to an amino group of a drug to form a carbamate linkage. The conjugation of the polymeric derivatives of the invention to a drug increases the water solubility of the drug, prolongs plasma half-life through, for example, reduced kidney clearance and protection towards degrading enzymes, and prevents or reduces aggregation, immunogenicity, and antigenicity. Advantageously, the polymeric derivative can be released in vivo to result in the drug in its native form, maintaining the efficacy of the drug. Also advantageously, and without intending to be bound by any particular theory, the release mechanism of the disclosed polymeric derivatives occurs through a multi-step process, wherein the hydrolysis of the carbamate linkage is not the rate-determining step of the process. Instead, the rate-determining step of the reaction is the hydrolysis of an ester moiety that can be tailored to achieve faster or slower hydrolysis by manipulating the steric hindrance and/or the electronic effects near the carbonyl carbon of the ester. Thus, the rate of release of the drug can be tailored to a specific therapeutic design.

Disclosed herein are polymeric derivatives of the general Formula I:

Formula I

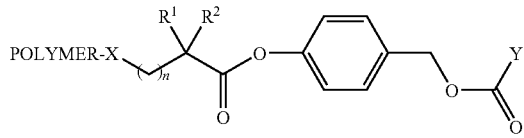

wherein Y is an activating group capable of being readily displaced by an amino group on a drug to form a carbamate linkage;

n is ≥1;

X is selected from the group consisting of O, S and $NR^3$, wherein $R^3$ is selected from the group consisting of hydrogen, ($C_1$-$C_6$)-alkyl, ($C_1$-$C_6$)-alkylenearyl, and aryl;

POLYMER is a water soluble, non-peptidic polymer; and $R^1$ and $R^2$ are independently selected from the group consisting of hydrogen, ($C_1$-$C_6$)-alkyl, ($C_1$-$C_6$)-alkylenearyl, and aryl.

The polymeric derivatives can be used to prepare drug conjugates of general Formula II:

Formula II

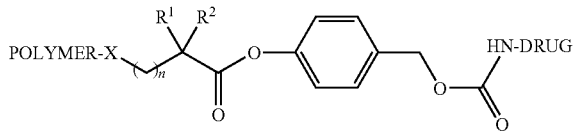

wherein POLYMER, X, $R^1$, $R^2$, and n are defined as in Formula I. DRUG is an amino-containing molecule, peptide, or protein capable of triggering a biological response, or a molecule, peptide, or protein capable of triggering a biological response that is modified to comprise an amino group. DRUG contains one or more amino groups for reaction, therefore one or more groups can be reacted with the polymeric derivative.

"Drug" refers to an amino containing molecule, peptide, or protein that triggers a biological response, or a molecule, peptide, or protein that triggers a biological response and is modified to comprise an amino group.

"($C_1$-$C_6$)-alkyl" refers to monovalent alkyl groups having 1 to 6 carbon atoms. This term is exemplified by groups such as methyl, ethyl, propyl, butyl, hexyl and the like. Linear and branched alkyls are included. Alkyl groups optionally can be substituted, for example, with hydroxy (OH), halo, aryl, and amino.

As used herein, the term "alkylene" refers to an alkyl group having a substituent. For example, the term "alkylenearyl" refers to an alkyl group substituted with an aryl group.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

"Activating group" (Y) refers to a moiety that is displaced from a carbonyl as a result of an acyl substitution reaction. For example, an amino group of a drug can displace an activating group attached to a carbonyl to form a carbamate linkage, as shown below:

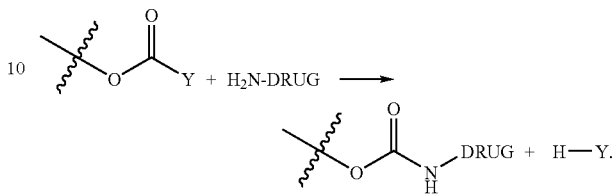

Specific activating groups contemplated include, but are not limited to, halide, $-N_3$, $-CN$, RO$-$, $NH_2O-$, NHRO$-$, $NR_2O-$, $RCO_2-$, $ROCO_2-$, $RNCO_2-$, RS$-$, RC(S)O$-$, $RCS_2-$, RSC(O)S$-$, $RSCS_2-RSCO_2-$, ROC(S)O$-$, $ROCS_2-$, $RSO_2-$, $RSO_3-$, $ROSO_2-$, $ROSO_3-$, $RPO_3-$, $ROPO_3-$, imidazolyl, N-triazolyl, N-benzotriazolyl, benzotriazolyloxy, imidazolyloxy, N-imidazolinone, N-imidazolone, N-imidazolinethione, N-succinimidyl, N-phthalimidyl, N-succinimidyloxy, N-phthalimidyloxy, N-(5-norbornen-2,3-dicarboxylmidyloxy), 2-thioxothiazolidine-3-yl, $-ON=C(CN)R$, 2-pyridyloxy, phenoxy, or substituted phenoxy (e.g. p-chlorophenoxy, p-nitrophenoxy, trichlorophenoxy, pentachlorophenoxy), wherein R is an alkyl group (unsubstituted or substituted) or an aryl group (unsubstituted or substituted), or other suitable activating group apparent to those of ordinary skill. In a preferred embodiment, the activating group is selected from the group consisting of N-succinimidyloxy, 1-benzotriazolyloxy, N-phthalimidyloxy, N-(5-norbornen-2,3-dicarboxylmidyloxy), p-nitrophenoxy, 2-thioxothiazolidine-3-yl, and imidazolyl.

A "water soluble polymer" refers to a hydrophilic, non-peptidic homopolymer or copolymer. The term "water soluble polymer" includes linear or branched polymers such as poly(alkylene glycol), water soluble polyphosphazenes or carbohydrate-based polymers such as polysaccharides. The water soluble polymer can also be end-capped. Non-limiting examples of water soluble polymers contemplated include polyethylene glycol (PEG), branched PEG, polysialic acid (PSA), polysaccharides, pullulane, chitosan, hyaluronic acid, chondroitin sulfate, dermatan sulfate, starch, dextran, carboxymethyl-dextran, polyalkylene oxide (PAO), copolymers of polyalkylene oxides, polyoxamer (such as PLURONIC®), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyethylene-co-maleic acid anhydride, polystyrene-co-maleic acid anhydride, poly(1-hydroxymethylethylene hydroxymethylformal) (PHF), and 2-methacryloyloxy-2'-ethyltrimethylammonium phosphate (MPC). The water soluble polymer can have a molecular weight of from about 200 to about 500,000. In some embodiments, the water soluble polymer has a molecular weight of from about 1,000 to about 25,000 or from about 40,000 to about 60,000. In a specific embodiment, the water soluble polymer has a molecular weight of from about 2,000 to about 10,000.

In some embodiments, the water soluble polymer is a PEG, which can be linear or branched. PEG can have a molecular weight of about 200 to about 500,000, such as about 1000 to about 25,000, about 2000 to about 10,000, or about 40,000 to about 60,000. In a specific embodiment, PEG can have a molecular weight of about 2000. Specific PEG polymers contemplated include PEG 200, PEG 300, PEG 2000, PEG 3350, PEG 8000, PEG 10,000 and PEG 20,000.

In some embodiments, the water soluble polymer is a block polymer of PEG and other poly(alkylene glycols), such as PLURONIC® F127 or PLURONIC® F68.

In various embodiments, the water soluble polymer is a polysaccharide, such as a PSA derivative. The polysaccharide can comprise between 2 and 200 units of a monosaccharide, such as 10 to 100 units of a monosaccharide and/or at least 3 units of a monosaccharide.

"Releasable" polymeric derivative refers to a polymeric derivative, which is bound to an amino-containing drug to form a conjugate, wherein the polymeric derivative is released in vivo, yielding the drug in its native form. Synonyms for releasable are "degradable" or "hydrolyzable."

Variable n is ≥1. In one embodiment, n is an integer between 1 and 10, and all subranges therein. In a specific embodiment, n is selected from the group consisting of 1, 2, 3, 4, and 5.

Variable X is selected from the group consisting of O, S and $NR^3$, wherein $R^3$ is hydrogen or $(C_1-C_6)$-alkyl, $(C_1-C_6)$-alkylenearyl, and aryl. In one embodiment, X is O. In another embodiment, X is NH.

$R^1$ and $R^2$ are independently selected from the group consisting of hydrogen, $(C_1-C_6)$-alkyl, $(C_1-C_6)$-alkyl, $(C_1-C_6)$-alkylenearyl, and aryl. $R^1$ and $R^2$ can be independently either hydrogen or $(C_1-C_6)$-alkyl. Specifically contemplated $R^1$ and $R^2$ include hydrogen, methyl, ethyl, n-propyl, isopropyl and n-butyl. In a specific embodiment, $R^1$ is hydrogen and $R^2$ is $(C_1-C_6)$-alkyl. For example, $R^1$ is hydrogen and $R^2$ is methyl.

Examples of DRUG that are contemplated include, but are not limited to, natural enzymes, proteins derived from natural sources, recombinant proteins, natural peptides, synthetic peptides, cyclic peptides, antibodies, receptor agonists, cytotoxic agents, immunoglobins, beta-adrenergic blocking agents, calcium channel blockers, coronary vasodilators, cardiac glycosides, antiarrhythmics, cardiac sympathomemetics, angiotensin converting enzyme (ACE) inhibitors, diuretics, inotropes, cholesterol and triglyceride reducers, bile acid sequestrants, fibrates, 3-hydroxy-3-methylgluteryl (HMG)-CoA reductase inhibitors, niacin derivatives, antiadrenergic agents, alpha-adrenergic blocking agents, centrally acting antiadrenergic agents, vasodilators, potassium-sparing agents, thiazides and related agents, angiotensin II receptor antagonists, peripheral vasodilators, antiandrogens, estrogens, antibiotics, retinoids, insulins and analogs, alpha-glucosidase inhibitors, biguanides, meglitinides, sulfonylureas, thizaolidinediones, androgens, progestogens, bone metabolism regulators, anterior pituitary hormones, hypothalamic hormones, posterior pituitary hormones, gonadotropins, gonadotropin-releasing hormone antagonists, ovulation stimulants, selective estrogen receptor modulators, antithyroid agents, thyroid hormones, bulk forming agents, laxatives, antiperistaltics, flora modifiers, intestinal adsorbents, intestinal anti-infectives, antianorexic, anticachexic, antibulimics, appetite suppressants, antiobesity agents, antacids, upper gastrointestinal tract agents, anticholinergic agents, aminosalicylic acid derivatives, biological response modifiers, corticosteroids, antispasmodics, 5-HT$_4$ partial agonists, antihistamines, cannabinoids, dopamine antagonists, serotonin antagonists, cytoprotectives, histamine H2-receptor antagonists, mucosal protective agent, proton pump inhibitors, H. pylori eradication therapy, erythropoieses stimulants, hematopoietic agents, anemia agents, heparins, antifibrinolytics, hemostatics, blood coagulation factors, adenosine diphosphate inhibitors, glycoprotein receptor inhibitors, fibrinogen-platelet binding inhibitors, thromboxane-$A_2$ inhibitors, plasminogen activators, antithrombotic agents, glucocorticoids, mineralcorticoids, corticosteroids, selective immunosuppressive agents, antifungals, drugs involved in prophylactic therapy, AIDS-associated infections, cytomegalovirus, non-nucleoside reverse transcriptase inhibitors, nucleoside analog reverse transcriptse inhibitors, protease inhibitors, anemia, Kaposi's sarcoma, aminoglycosides, carbapenems, cephalosporins, glycopoptides, lincosamides, macrolies, oxazolidinones, penicillins, streptogramins, sulfonamides, trimethoprim and derivatives, tetracyclines, anthelmintics, amebicies, biguanides, cinchona alkaloids, folic acid antagonists, quinoline derivatives, *Pneumocystis carinii* therapy, hydrazides, imidazoles, triazoles, nitroimidzaoles, cyclic amines, neuraminidase inhibitors, nucleosides, phosphate binders, cholinesterase inhibitors, adjunctive therapy, barbiturates and derivatives, benzodiazepines, gamma aminobutyric acid derivatives, hydantoin derivatives, iminostilbene derivatives, succinimide derivatives, anticonvulsants, ergot alkaloids, antimigrane preparations, biological response modifiers, carbamic acid eaters, tricyclic derivatives, depolarizing agents, nondepolarizing agents, neuromuscular paralytic agents, CNS stimulants, dopaminergic reagents, monoamine oxidase inhibitors, COMT inhibitors, alkyl sulphonates, ethylenimines, imidazotetrazines, nitrogen mustard analogs, nitrosoureas, platinum-containing compounds, antimetabolites, purine analogs, pyrimidine analogs, urea derivatives, antracyclines, actinomycinds, camptothecin derivatives, epipodophyllotoxins, taxanes, vinca alkaloids and analogs, antiandrogens, antiestrogens, nonsteroidal aromatase inhibitors, protein kinase inhibitor antineoplastics, azaspirodecanedione derivatives, anxiolytics, stimulants, monoamind reuptake inhibitors, selective serotonin reuptake inhibitors, antidepressants, benzisooxazole derivatives, butyrophenone derivatives, dibenzodiazepine derivatives, dibenzothiazepine derivatives, diphenylbutylpiperidine derivatives, phenothiazines, thienobenzodiazepine derivatives, thioxanthene derivatives, allergenic extracts, nonsteroidal agents, leukotriene receptor antagonists, xanthines, endothelin receptor antagonist, prostaglandins, lung surfactants, mucolytics, antimitotics, uricosurics, xanthine oxidase inhibitors, phosphodiesterase inhibitors, metheamine salts, nitrofuran derivatives, quinolones, smooth muscle relaxants, parasympathomimetic agents, halogenated hydrocarbons, esters of amino benzoic acid, amides (e.g. lidocaine, articaine hydrochloride, bupivacaine hydrochloride), antipyretics, hynotics and sedatives, cyclopyrrolones, pyrazolopyrimidines, nonsteroidal anti-inflammatory drugs, opioids, para-aminophenol derivatives, alcohol dehydrogenase inhibitor, heparin antagonists, adsorbents, emetics, opoid antagonists, cholinesterase reactivators, nicotine replacement therapy, vitamin A analogs and antagonists, vitamin B analogs and antagonists, vitamin C analogs and antagonists, vitamin D analogs and antagonists, vitamin E analogs and antagonists, vitamin K analogs and antagonists.

In some embodiments, DRUG is a protein, antibody, or molecule. In some specific embodiments, DRUG is neocarzinostatin, zinostatin, adenosine deaminase, asparaginase, interferon α2b, interferon α2a, growth hormone receptor agonist, granulocyte colony-stimulating factor (G-CSF), anti-vasco endothelial growth factor (VEGF) aptamer, anti-tumor necrosis factor (TNF) Fab, diFab antibody, doxorubicin, doxorubicin-galactosamine, camptothecin, paclitaxel, a platinate, erythropoietins, Factor H, Factor VIII (FVIII), von Willebrand Factor (vWF), Factor VIIa (FVIIa), or Factor IX (FIX). (See, e.g., Pasut et al. *Prog. In Polymer Science,* 2007, 32, 933-961, which is incorporated herein by reference in its entirety.) In specific embodiments DRUG is a plasma protein or blood coagulation factor such as, for example, erythropoietin, Factor H, Factor VIII (FVIII), von Willebrand Factor (vWF), Factor VIIa (FVIIa), Factor IX (FIX) and the like.

The polymeric derivatives of general Formula IA can be those as recited in Table 1.

TABLE 1

Formula IA

POLYMER-O—(CR$^1$R$^2$)$_n$—C(O)—O—C$_6$H$_4$—CH$_2$—O—C(O)—O—NHS

| Compound IA | N | R$^1$ | R$^2$ |
|---|---|---|---|
| i | 2 | Me | H |
| ii | 2 | Me | Me |
| iii | 3 | Me | Me |
| iv | 4 | Me | Me |
| v | 3 | Et | H |
| vi | 3 | n-Pr | H |
| vii | 2 | n-Bu | H |
| viii | 1 | Me | Me |
| ix | 1 | Me | Et |
| x | 1 | Et | Et |
| xi | 1 | Me | n-Pr |
| xii | 1 | n-Pr | n-Pr |
| xiii | 1 | iso-Pr | H |
| xiv | 1 | n-Bu | H |
| xv | 1 | H | Me |

Abbreviations used in the specification and claims are defined in Table 2. Additional abbreviations are found throughout the specification.

TABLE 2

| Abbreviation | Name |
|---|---|
| NH$_4$OH | Ammonium hydroxide |
| tBuOH | tert-Butanol |
| TBME | tert-Butyl methyl ether |
| DBU | 1,8-Diazabicyclo[5.4.0]undec-7-ene |
| DCC | N,N-Dicyclohexylcarbodiimide |
| DCM | Dichloromethane |
| DIPEA | Diisopropylethylamine |
| DIPA | Diisopropylamine |
| DMAP | 4-Dimethylaminopyridine |
| DMF | Dimethylformamide |
| DSC | N,N'-Disuccinimidyl carbonate |
| EDC | 1-Ethyl-3-(3-dimethylaminopropyl)carbodiimide |
| FVIIa | Factor VIIa |
| FVIII | Factor VIII |
| FIX | Factor IX |
| HCl | Hydrochloric acid |
| HES | Hydroxyethyl starch |
| NHS | N-Hydroxysuccinimide |
| MsCl | Methanesulfonyl chloride |
| OMs | Methylsulfonyl (Mesyl) |
| MW | Molecular weight |
| mPEG | Monomethoxy polyethylene glycol |
| PBr$_3$ | Phosphorus tribromide |
| PEG | Polyethylene glycol |
| PSA | Polysialic acid |
| PVP | Polyvinylpyrrolidone |
| SDS-PAGE | Sodium dodecyl sulfate polyacrylamide gel electrophoresis |
| NaHCO$_3$ | Sodium bicarbonate |
| NaCl | Sodium chloride |
| NaH | Sodium hydride |
| NaOH | Sodium hydroxide |
| Na$_2$SO$_4$ | Sodium sulfate |
| TLC | Thin layer chromatography |
| TEA | Triethylamine |
| TFA | Trifluoroacetic acid |
| THF | Tetrahydrofuran |
| TMS | Tetramethylsilane |
| vWF | von Willebrand factor |

In another aspect, the invention relates to the preparation of polymeric derivatives of Formula I. A synthetic protocol for the preparation of these derivatives is shown in Scheme 1, wherein "Halogen" is selected from the group consisting of I, Br, and Cl, and variables n, R$^1$, R$^2$ and POLYMER-XH are as described herein.

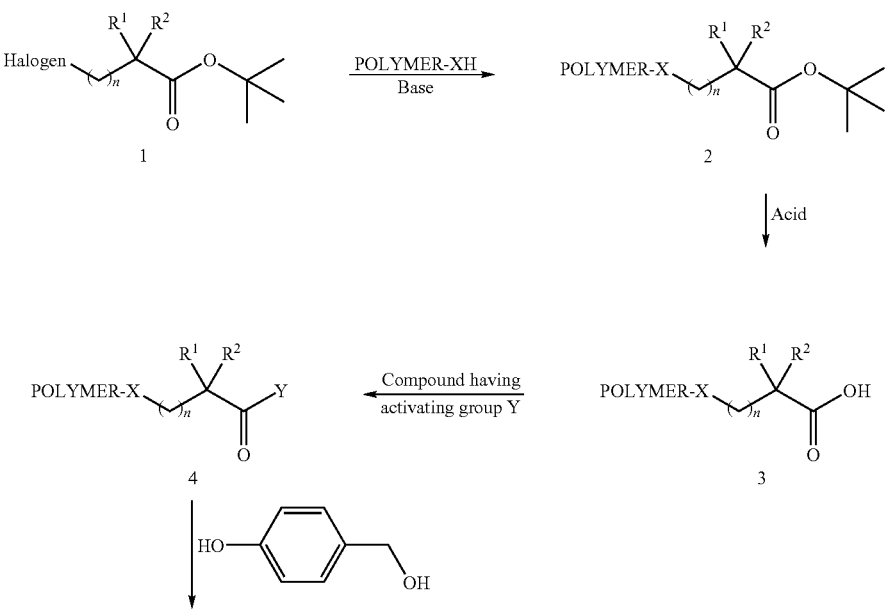

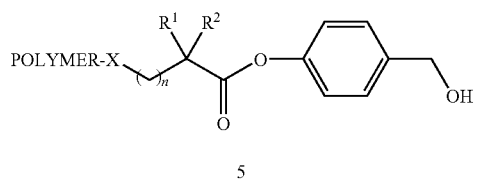 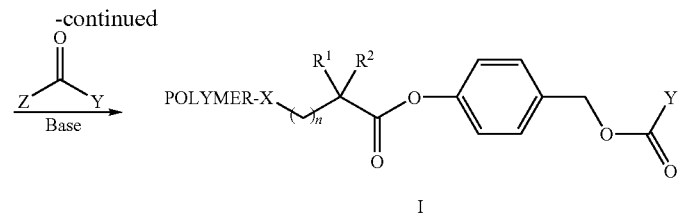

In the first step of the synthesis, compound 1 reacts with POLYMER-XH in the presence of a base to form compound 2. Suitable bases include inorganic bases (e.g. cesium carbonate and the like), alkali metal hydrides (e.g. sodium hydride and the like), alkoxides (e.g. potassium tert-butoxide), and the like.

In the second step of the synthesis, compound 2 is deprotected in the presence of an acid to form compound 3. Suitable acids include trifluoroacetic acid (TFA), hydrochloric acid (HCl) and the like. In the third step of the synthesis, carboxylic acid compound 3 is reacted with a compound having an activating group (Y) to form compound 4. Suitable compounds having activating groups include thioxothazolidines and succinimidyl esters, and other compounds having "activating groups" as defined below. The Y activating group is displaced with 4-hydroxybenzyl alcohol in the fourth step of the synthesis to form compound 5. In the final step of the synthesis, compound 5 is subjected to a coupling reaction with a diactivated carbonyl compound under basic conditions to yield the polymeric derivative I.

Activating group Y and Z and Y on the diactivated carbonyl compound are activating groups independently selected from the group consisting of halide, —N$_3$, —CN, RO—, NH$_2$O—, NHRO—, NR$_2$O—, RCO$_2$—, ROCO$_2$—, RNCO$_2$—, RS—, RC(S)O—, RCS$_2$—, RSC(O)S—, RSCS$_2$—RSCO$_2$—, ROC(S)O—, ROCS$_2$—, RSO$_2$—, RSO$_3$—, ROSO$_2$—, ROSO$_3$—, RPO$_3$—, ROPO$_3$—, imidazolyl, N-triazolyl, N-benzotriazolyl, benzotriazolyloxy, imidazolyloxy, N-imidazolinone, N-imidazolone, N-imidazolinethione, N-succinimidyl, N-phthalimidyl, N-succinimidyloxy, N-phthalimidyloxy, N-(5-norbornen-2,3-dicarboxylmidyloxy), 2-thioxothiazolidine-3-yl, —ON=C(CN)R, 2-pyridyloxy, phenoxy, or substituted phenoxy (e.g. p-chlorophenoxy, p-nitrophenoxy, trichlorophenoxy, pentachlorophenoxy), wherein R is an alkyl group (unsubstituted or substituted) or an aryl group (unsubstituted or substituted), or other suitable activating groups apparent to those of ordinary skill.

The base in the final step of the synthesis is any base that is capable of catalyzing the reaction. Preferably the base is an organic base. Non-limiting examples of organic bases include, for example, trialkylamines and selected nitrogen heterocycles. Specific organic bases contemplated are triethylamine (TEA), dimethylaminopyridine (DMAP), pyridine, N,N-diisopropylethylamine (DIPEA), and 1,8-diazabicyclo[5.4.0]undec-7-ene (DBU).

In some embodiments, Z and Y are as described in Table 3.

TABLE 3

| | Z | Y |
|---|---|---|
| a | N-Succinimidyloxy | N-Succinimidyloxy |
| b | 1-Benzotriazolyloxy | 1-Benzotriazolyloxy |
| c | N-Phthalimidyloxy | N-Phthalimidyloxy |
| d | N-(5-Norbornen-2,3-dicarboxyimidyloxy) | N-(5-Norbornen-2,3-dicarboxyimidyloxy) |
| e | Cl | p-Nitrophenoxy |
| f | Cl | 2-Thioxothiazolidine-3-yl |
| g | Cl | Imidazolyl |

In some embodiments, the polymeric derivative of Formula I can be prepared according to Scheme 2, wherein "Halogen" is selected from the group consisting of I, Br, and Cl, and variables n, R$^1$, R$^2$, Y and Z are as defined herein.

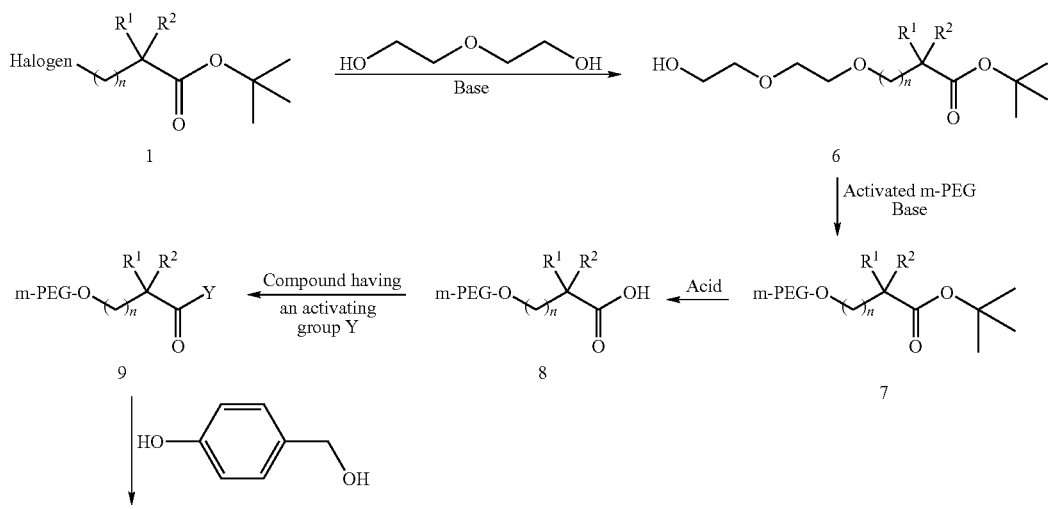

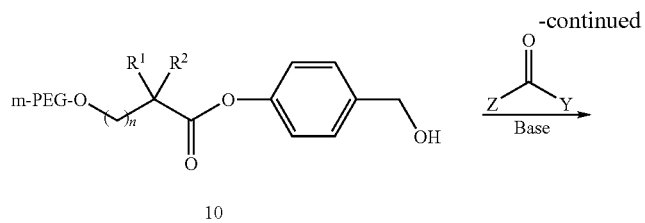
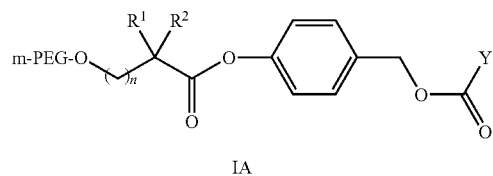

In the first step of the synthesis, compound 1 reacts with diethylene glycol in the presence of a base to form compound 6. Suitable bases include alkali metal hydrides (such as sodium hydride, potassium hydride, and the like), bulky amides (such as lithium diisopropylamide (LDA) and the like), trialkylamines (such as DIPEA, TEA, and the like), alkoxides (such as potassium tert-butoxide and the like), and inorganic bases (such as cesium hydroxide, cesium carbonate and the like).

In the second step of the synthesis, the diethylene glycol moiety of compound 6 is lengthened through a nucleophilic substitution reaction with a sulfonate ester-activated monomethoxy poly(ethylene glycol) to form compound 7 (see e.g. International Publication No. WO 2006/099794). Suitable sulfonate ester activating groups are, for example, methyl sulfonate (mPEG-OMs), fluorophenylsulfonate (mPEG-OTs), triflate, tosylate, and the like. In the third step of the synthesis, compound 7 is deprotected in the presence of an acid to form carboxylic acid compound 8. Suitable acids include trifluoroacetic acid (TFA), hydrochloric acid (HCl), and the like. In the fourth step of the synthesis, compound 8 is reacted with a compound having an activating group (Y) to form compound 9. Suitable compounds are those having activating groups as described herein, such as, for example, N-succinimidyloxy, 1-benzotriazolyloxy, N-phthalimidyloxy, N-(5-norbornen-2,3-dicarboxylmidyloxy), p-nitrophenoxy, 2-thioxothiazolidine-3-yl, and imidazolyl. The activating group Y on compound 9 is displaced with 4-hydroxybenzyl alcohol in the fifth step of the synthesis to form compound 10. In the final step of the synthesis, compound 10 is subjected to a coupling reaction with a diactivated carbonyl, such as any diactivated carbonyl compound described herein or listed in Table 3 (e.g. N,N'-disuccinimidyl carbonate (DSC), compounds b, c, and d in Table 3) and a base to yield the polymeric derivative IA. Suitable bases include any base that is capable of catalyzing the reaction, such as trialkylamines and selected nitrogen heterocycles (e.g. triethylamine (TEA), dimethylaminopyridine (DMAP), pyridine, N,N-diisopropylethylamine (DIPEA), and 1,8-diazabicyclo[5.4.0]undec-7-ene (DBU) and the like).

Examples of Compounds 1 and IA of Scheme 2 are shown in Table 4.

TABLE 4

| | Compound 1 | Compound IA |
|---|---|---|
| i | | |
| ii | | |
| vii | | |

TABLE 4-continued
| Compound 1 | Compound IA |
|---|---|
| xiv | |
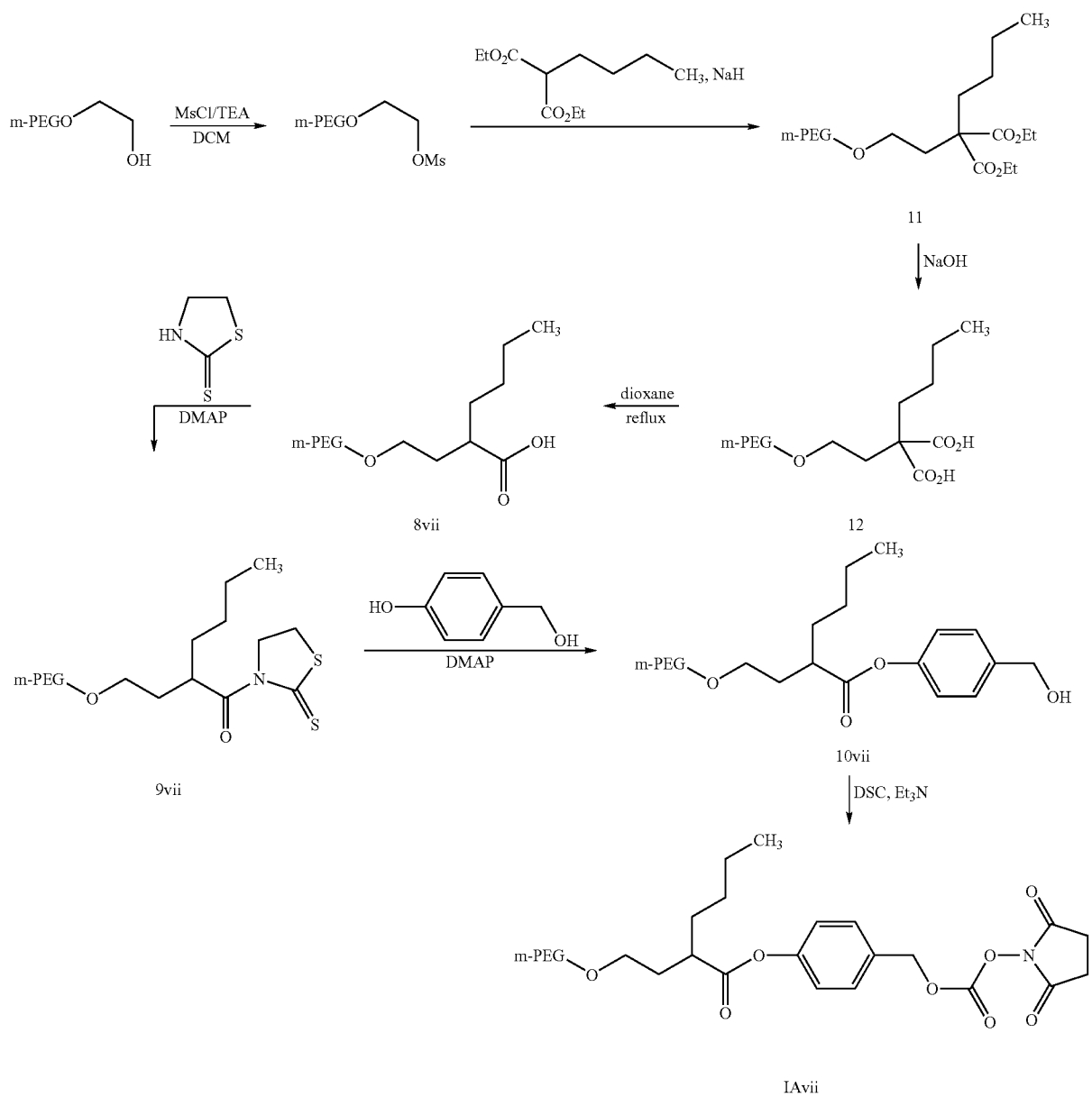
In a specific embodiment, a synthetic protocol for the formation of polymeric derivative IAvii from Table 4 is shown in Scheme 3.

In the first step of the synthesis, methoxy PEG is activated with methanesulfonyl chloride to form monomethoxy poly (ethylene glycol) methanesulfonate (mPEG-OMs). In the second step of the synthesis, mPEG-OMs is treated with diethyl butylmalonate and a base. Suitable bases include alkali metal hydrides (such as sodium hydride, potassium hydride, and the like), bulky amides (such as lithium diisopropylamide (LDA) and the like), trialkylamines (such as DIPEA, TEA, and the like), alkoxides (such as potassium tert-butoxide and the like), and inorganic bases (such as cesium hydroxide, cesium carbonate and the like) to form compound 11, which is hydrolyzed in the presence of a base, such as alkali metal hydroxides (e.g. sodium hydroxide, potassium hydroxide) in step 3 to form compound 12. Compound 12 undergoes decarboxylation under reflux conditions in step 4 to form compound 8vii, which is activated with a 2-thioxothiazolidine-3-yl moiety in step 5 to form 9vii. The thiazolidine moiety on 9vii is displaced with 4-hydroxybenzyl alcohol in the sixth step of the synthesis to form compound 10vii. In the final step of the synthesis, compound 10vii is subjected to a coupling reaction with a diactivated carbonyl, such as N,N'-disuccinimidyl carbonate (DSC) or the compounds listed in Table 3 (e.g. b, c and d) in the presence of a base to provide the polymeric derivative IAvii. Suitable bases include any base that is capable of catalyzing the reaction, such as trialkylamines and selected nitrogen heterocycles (e.g. triethylamine (TEA), dimethylaminopyridine (DMAP), pyridine, N,N-diisopropylethylamine (DIPEA), and 1,8-diazabicyclo[5.4.0]undec-7-ene (DBU) and the like), such as a trialkyl amine (such as DIPEA, TEA, or the like.

In another specific embodiment, a synthetic protocol for the preparation of polymeric derivative IAi from Table 4 is shown in Scheme 4.

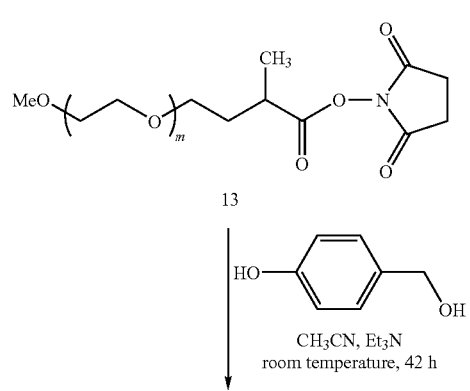

Scheme 4

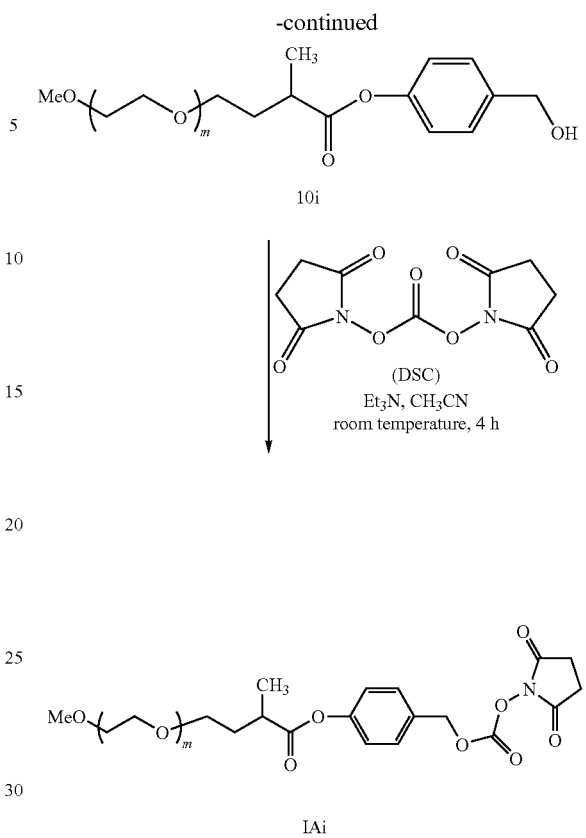

In Scheme 4, m is defined as the number of monomeric units and has a range of values consistent with the molecular weight distribution, such as an integer of 4 to 11,000, or 20 to 500.

One polymeric derivative (IAi), with m approximately 40, is synthesized according to Scheme 4 as follows. The N-succinimidyl ester, 13, is transesterified with 4-hydroxybenzyl alcohol under basic conditions to yield the 4-hydroxymethylphenyl ester, 10i. Compound 10i is treated with N,N-disuccinimidyl carbonate (DSC) under basic conditions according to the method of Ghosh et al. (*Tetrahedron Lett.* 33, 2781-2784 (1992)). An aqueous bicarbonate work-up, followed by two recrystallizations from chloroform/ether, yield IAi as a white solid. The details of the synthetic procedures and the characterization of compounds are further described in Example 5.

In another aspect of the invention, methods for the preparation of compounds of Formula II are disclosed. Compounds of Formula II can be prepared by reacting compounds of Formula I with a drug.

Drugs conjugated to the polymeric derivative as shown in Formula II have a significantly increased half-life, improved solubility, and reduced degradation by proteolytic enzymes. The subsequent release of the polymeric derivative from the drug conjugate allows the activity of the drug to be regained, yielding the drug in its native form. It is theorized that the release of the polymeric derivative from the drug conjugate follows a multi-step release mechanism as shown in Scheme 5, wherein variables $R^1$, $R^2$, POLYMER, X and DRUG are as defined in Formula II.

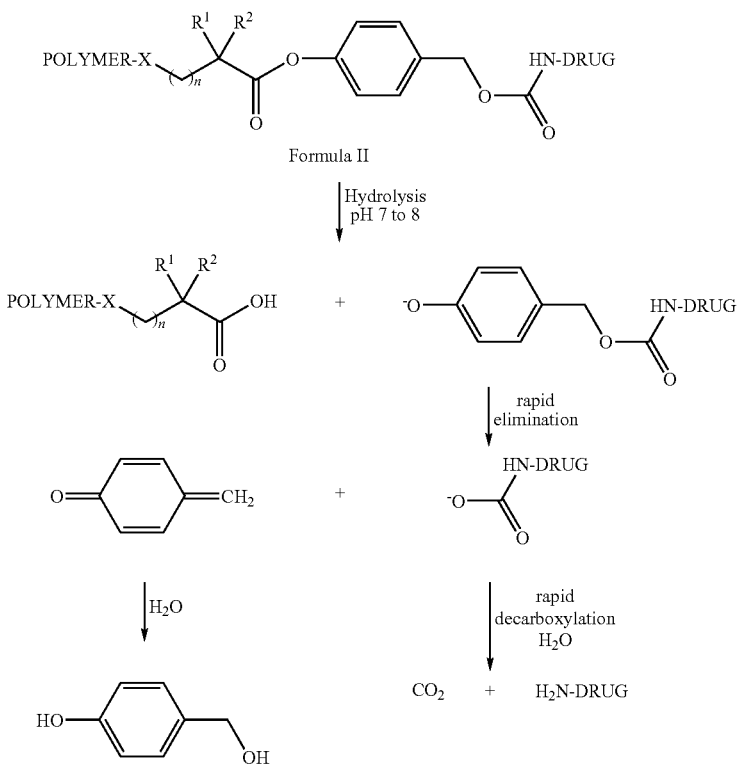

Scheme 5

Formula II

The first hydrolysis step of Scheme 5 is the rate-determining step of the reaction. Therefore, the rate of cleavage of the polymeric derivative from the drug conjugate can be tailored by manipulating the electronics effects and steric hindrance near the electrophilic carbon of the ester.

The rate of cleavage of the polymeric derivative from the drug conjugate can be increased by decreasing the electron density at the carbonyl carbon of the ester through inductive effects. The electron density at the carbonyl carbon of the ester can be decreased by positioning the electronegative atom X closer to the carbonyl carbon of the ester. For example, a faster hydrolysis reaction occurs when n=1 than when n=2. The electron density at the carbonyl carbon of the ester can additionally or alternatively be decreased by increasing the electronegativity of atom X. For example, a faster hydrolysis reaction occurs when X is oxygen than when X is nitrogen.

The electron density at the carbonyl carbon of the ester can additionally or alternatively be decreased by increasing the electronegativity of $R^1$ and/or $R^2$. For example, a faster hydrolysis reaction occurs when $R^1$ is aryl than when $R^1$ is alkyl. The electron density at the carbonyl carbon of the ester can additionally or alternatively be decreased when $R^1$ and/or $R^2$ are substituted with one or more electron withdrawing moieties. For example, a faster hydrolysis reaction occurs when $R^1$ is —$CH_2F$ than when $R^1$ is —$CH_3$. Some examples of substituents on $R^1$ and/or $R^2$ that can increase the rate of hydrolysis include fluoro, chloro, bromo, hydroxyl, alkoxyl, amino, alkenyl, alkynyl, nitro, cyano, carbonyl, and aryl. The electron density at the carbonyl carbon of the ester can additionally or alternatively be decreased by increasing the number of electron withdrawing substituents on $R^1$ and/or $R^2$. For example, a faster hydrolysis reaction occurs when $R^1$ is —$CF_3$ than when $R^1$ is —$CHF_2$. The electron density at the carbonyl carbon of the ester can additionally or alternatively be decreased by moving an electron withdrawing moiety on $R^1$ and/or $R^2$ closer to the carbonyl carbon of the ester. For example, a faster hydrolysis reaction occurs when $R^1$ is 1-fluoroethyl than when $R^1$ is 2-fluoroethyl.

The rate of cleavage of the polymeric derivative from the drug conjugate can be decreased by increasing the electron density at the carbonyl carbon of the ester through inductive effects. The electron density at the carbonyl carbon of the ester can be decreased by positioning the electronegative atom X further away from the carbonyl carbon of the ester. For example, a slower hydrolysis reaction occurs when n=2 than when n=1. The electron density at the carbonyl carbon of the ester can additionally or alternatively be increased by decreasing the electronegativity of atom X. For example, a slower hydrolysis reaction occurs when X is nitrogen than when X is oxygen.

The electron density at the carbonyl carbon of the ester can additionally or alternatively be increased by increasing the electron donating ability of $R^1$ and/or $R^2$. For example, a slower hydrolysis reaction occurs when $R^1$ is —$CH_3$ than when $R^1$ is —H. The electron density at the carbonyl carbon of the ester can additionally or alternatively be increased when $R^1$ and/or $R^2$ are substituted with one or more electron donating moieties. For example, a slower hydrolysis reaction occurs when $R^1$ is substituted with —$CH_3$ than with —$CF_3$, and when $R^1$ is substituted with —$CH_3$ than with —H. An alkyl group (e.g. ethyl, n-propyl, isopropyl, n-butyl, s-butyl, and t-butyl) is one example of a type of substituent on $R^1$ and/or $R^2$ that can decrease the rate of hydrolysis when compared to hydrogen. The electron density at the carbonyl carbon of the ester can additionally or alternatively be increased when the number of electron donating substituents on $R^1$ and/or $R^2$ is increased. For example, a slower hydrolysis reaction occurs when $R^1$ is substituted with two methyl groups than when $R^1$ is substituted with one methyl group. The electron density at the carbonyl carbon of the ester can additionally or alternatively be increased by moving an electron withdrawing moiety on $R^1$ and/or $R^2$ further from carbonyl carbon of the ester. For example, a slower hydrolysis reaction occurs when $R^1$ is 2-fluoroethyl than when $R^1$ is 1-fluoroethyl.

The rate of cleavage of the polymeric derivative from the drug conjugate can be decreased by increasing the steric hindrance at the carbonyl carbon of the ester through increasing the bulkiness of $R^1$ and/or $R^2$ on the alpha carbon to the ester. For example, a slower hydrolysis reaction occurs when $R^1$ is —$CH_3$ and $R^2$ is H, than when $R^1=R^2=H$. A slower hydrolysis also occurs when $R^1$ is n-butyl and $R^2$ is H, than when $R^1$ is n-propyl and $R^2$ is H. The steric hindrance at the carbonyl carbon of the ester can additionally or alternatively be increased by increasing the number of substituents on the alpha carbon to the ester. For example, a slower hydrolysis reaction occurs when the alpha carbon to the ester is substituted with two methyl groups (e.g. $R^1=R^2=CH_3$) than with one methyl group ($R^1=CH_3$, $R^2=H$).

The rate of cleavage of the polymeric derivative from the drug conjugate can be increased by decreasing the steric hindrance at the carbonyl carbon of the ester through decreasing the bulkiness of $R^1$ and/or $R^2$ on the alpha carbon to the ester. For example, a faster hydrolysis reaction occurs when $R^1=R^2=H$, than when $R^1$ is —$CH_3$ and $R^2$ is H. A faster hydrolysis also occurs when $R^1$ is n-propyl and $R^2$ is H, than when $R^1$ is n-butyl and $R^2$ is H. The steric hindrance at the carbonyl carbon of the ester can additionally or alternatively be decreased by decreasing the number of substituents on the alpha carbon to the ester. For example, a faster hydrolysis reaction occurs when the alpha carbon to the ester is substituted with one methyl group ($R^1=CH_3$, $R^2=H$) than with two methyl groups (e.g. $R^1=R^2R=CH_3$).

Additionally or alternatively, the release of the polymeric derivatives from the drug conjugate also can be tailored by adjusting the pH of the cleavage solution. For example, the rate of hydrolysis of the polymeric derivative from the drug conjugate is faster at a pH of 8.5 than at a pH of 7.5.

A further aspect of the invention is directed to a pharmaceutical composition that includes a drug conjugate of the present invention, together with a pharmaceutically acceptable excipient, such as a diluent or carrier. Pharmaceutical compositions suitable for use in the present invention include those wherein the drug conjugate can be administered in an effective amount to achieve its intended purpose. Administration of the drug conjugate can be via any route, such as oral, injection, inhalation, and subcutaneous. The formulation can be a liquid, suspension, tablet, capsule, microcapsule, and the like.

Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pa., 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the pharmacokinetic data obtainable through animal or human clinical trials.

The drug conjugates disclosed herein can be encapsulated in the form of a microparticle comprising a core and a coating associated with the microparticle core, wherein the core is comprised of the drug conjugate, and the coating is comprised of a surfactant, antibody, and/or any other suitable coating material known to those skilled in the art. The particles can be amorphous, semicrystalline, crystalline, or a combination thereof as determined by suitable analytical methods such as differential scanning calorimetry (DSC) or X-ray diffraction. Prior to administration, the particles can be homogenized through a homogenization process and/or a microprecipitation/homogenization process.

The coated microparticles can have an average effective particle size of about 1 nm to about 2 μm as measured by dynamic light scattering methods (e.g., photocorrelation spectroscopy, laser diffraction, low-angle laser light scattering (LALLS), medium-angle laser light scattering (MALLS)), light obscuration methods (Coulter method, for example), rheology, or microscopy (light or electron). The preferred average effective particle size depends on factors such as the intended route of administration, formulation, solubility, toxicity and bioavailability of the compound. Other suitable particle sizes include, but are not limited to, about 10 nm to about 1 μm, about 50 nm to about 500 nm, and/or about 100 nm to about 250 nm.

The coated microparticles can be solid or semi-solid particles comprising the drug conjugate disclosed herein. The coated particles generally consist of at least 5% (w/w) of the drug conjugate, for example, at least 10% (w/w), at least 25% (w/w), at least 50% (w/w), and/or at least 75% (w/w) or more of the drug conjugate.

The processes for preparing the drug conjugate core of the microparticles described herein can be accomplished through numerous techniques. A representative, but non-exhaustive, list of techniques for preparing the drug conjugate core of the microparticles includes energy addition techniques (e.g. cavitation, shearing, impact forces), precipitation methods (e.g. microprecipitation, emulsion precipitation, solvent-antisolvent precipitation, phase inversion precipitation, pH shift precipitation, infusion precipitation, temperature shift precipitation, solvent evaporation precipitation, reaction precipitation, compressed fluid precipitation, spraying into cryogenic fluids, protein nanosphere/microsphere precipitation), and additional methods for preparing particle dispersions of pharmaceutical compositions, all of which are described in U.S. patent application Ser. Nos. 12/398,894 and 12/467,230, filed on Mar. 5, 2009 and May 15, 2009, respectively, which are herein incorporated by reference.

The processes for coating the microparticles of this embodiment of the present invention can be accomplished through various techniques known to those skilled in the art. The coating can be associated with the particle through various associations, including covalent and/or non-covalent associations (e.g., covalent bonding, ionic interactions, electrostatic interactions, dipole-dipole interactions, hydrogen bonding, van der Waal's forces, hydrophobic/hydrophobic domain interactions, cross-linking, and/or any other interactions).

The coating can include a single surfactant, or a combination of surfactants. The surfactant can be selected from a variety of known anionic surfactants, cationic surfactants, zwitterionic surfactants, nonionic surfactants and surface active biological modifiers. Suitable surfactants include, but are not limited to, poloxamers, phospholipids, polyethylene glycol-conjugated phospholipids, and polysorbates. Alternatively, the coating can be substantially free of surfactant (e.g., less than 2 weight percent of surfactant, less than 1 weight percent of surfactant, or less than 0.5 weight percent of surfactant).

The phrases "pharmaceutically acceptable" and "pharmacologically acceptable" refer to compounds and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

Pharmaceutically acceptable acid addition salts include inorganic or organic acid salts. Examples of suitable acid salts include the hydrochlorides, acetates, citrates, salicylates, nitrates, phosphates.

The present invention is illustrated by the following examples without being limited thereto.

EXAMPLES

General Experimental Procedures

Thin layer chromography (TLC) was performed on Silica Gel 60 $F_{254}$ plates, 2.5×7.5 cm×250 μm (layer) (EMD Chemicals), using chloroform:methanol (7:1) as the developing solvent for compounds 13, 10i and IAi in Scheme 4. Spots were visualized by UV and iodine. Mass spectra were obtained by MALDI TOF MS using a 2,5-dihydroxybenzoic acid matrix in a Voyager DESTR TOF mass spectrometer operating in the positive ion mode. A dilute aqueous sodium bicarbonate solution (pH 8.26) was used in the work-up of IAi and was prepared by dissolving sodium bicarbonate (1.1 g) in water and diluting to a final volume of 250 mL. For all other compounds, TLC was performed as specifically indicated. Mass spectra of mPEG containing compounds were obtained by MALDI TOF MS using a 2,5-dihydroxybenzoic acid and 0.1 M KCl matrix in a Voyager DE STR TOF mass spectrometer or a Bruker Ultraflex III TOF/TOF mass spectrometer. Mass spectra of lower molecular weight compounds, except for 1ii, were obtained by ESI-MS using 0.1% formic acid in a Waters/Micromass Q-TOF micro mass spectrometer or a Waters/Micromass Q-TOF API US mass spectrometer. The mass spectrum for 1ii was obtained in methanol from the Waters/Micromass Q-TOF API US mass spectrometer. $^1$H-NMR were obtained using either a Bruker Avance 1400 or a Bruker Avance III 600 Spectrometer. All ppm values are with respect to residual $CHCl_3$ or DMSO.

Example 1

Syntheses of Compounds 1i, 1ii, 1vii, and 1xiv

Synthesis of tert-butyl 4-bromo-2-methylbutanoate (1i)

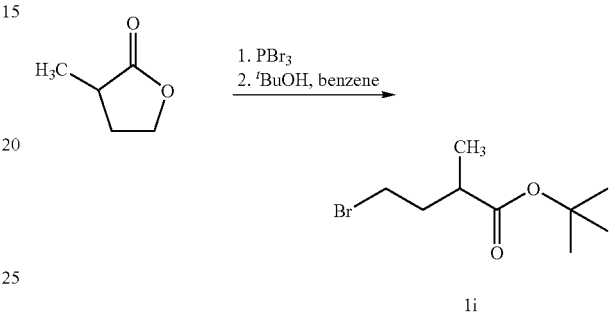

A mixture of α-methylbutyro-γ-lactone (86.5 g, 0.864 mol) and phosphorus tribromide ($PBr_3$) (86 mL, 0.912 mol) was stirred at 150 to 160° C. for 3 hours under argon. The mixture was cooled to ambient temperature and anhydrous benzene (400 mL) was added. The resulting mixture was heated to reflux for 5 minutes and cooled to ambient temperature. The supernatant of the mixture was carefully transferred to a dry addition funnel with the aid of additional anhydrous benzene (40 mL). The solution in the addition funnel was added quickly to tert-butanol (t-BuOH) (320 g, 4.32 mol) with rapid stirring, while maintaining the internal temperature at 15 to 30° C. by means of a room temperature water bath. After complete addition of the solution to t-BuOH, the resulting mixture was stirred for 30 minutes at ambient temperature, and was then poured into a mixture of water, tert-butyl methyl ether (TBME) and ice. The organic layer was separated, washed with ice cold water, and then washed multiple times with saturated aqueous sodium bicarbonate until the pH of the aqueous layer was 8 to 9. The organic layer was then washed with brine, dried over sodium sulfate, and concentrated to dryness. The residue was applied to a silica gel column and eluted with ethyl acetate (0 to 5%) in hexane. Appropriate fractions were combined and concentrated to afford 1i as a clear oil (58 g, 28% yield). $^1$H NMR ($CDCl_3$, δ): 1.17 (d), 1.48 (s), 1.90 (m), 2.23 (m), 2.59 (m), and 3.44 (m) ppm; $^{13}$C NMR ($CDCl_3$, δ): 17.0, 28.2, 31.2, 36.5, 39.1, 80.6, and 175.1 ppm; MS (TOF) ESI+: [M+Na]$^+$, 259.01, 261.02 Da.

Synthesis of tert-butyl 4-bromo-2,2-dimethylbutanoate (1ii)

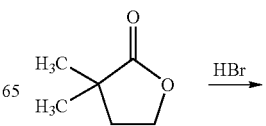

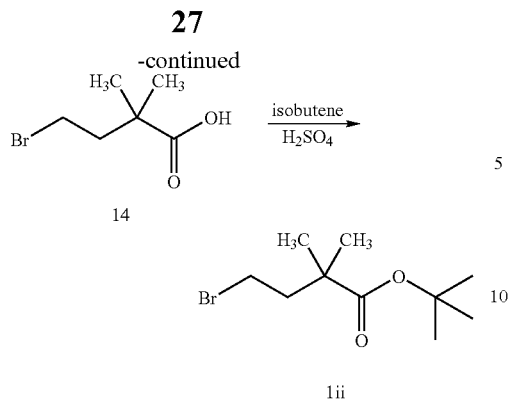

A flask containing α,α-dimethylbutyro-γ-lactone (50.67 g, 0.444 mol) at −78° C. was charged with HBr (38 g, 0.469 mol) while stirring. After the addition of HBr, the reaction mixture was allowed to warm to ambient temperature. The reaction solution turned into a purple solid and was dissolved in dichloromethane. The resulting solution was washed with brine, dried over sodium sulfate, and concentrated to dryness to give crude 14 as a slightly dark solid (90.8 g). Compound 14 was used for the next step of the reaction without further purification.

A mixture of 14 (50.8 g, 0.260 mol) and 95% sulfuric acid (5.0 g, 0.05 mol) was stirred in a lyophilizing vessel that had been placed in a stainless steel pressure vessel. The lyophilizing vessel served as a glass liner. The assembly was maintained at approximately −50° C. Isobutene (50 g, 0.893 mol) was added and the pressure vessel was sealed and allowed to reach ambient temperature. Stirring was continued at ambient temperature for 3 days. After that time, the pressure was carefully released, and the residue was diluted with tert-butyl methyl ether (TBME). The organic layer was separated and washed multiple times with ice cold aqueous sodium bicarbonate until the pH of the aqueous layer was 8 to 9. The organic layer was then washed with brine, dried over sodium sulfate and concentrated to dryness. The residue was applied to a silica gel column and eluted with dichloromethane (0 to 25%) in hexane. Appropriate fractions were combined and concentrated to afford 1ii as a clear oil (29.5 g, 45% overall yield for the two steps). In the process, 17 g of the starting material, α,α-dimethylbutyro-γ-lactone, was also recovered. The spectral data for 1ii are listed below. The mass spectrum was obtained from a fresh methanolic solution. $^1$H NMR (CDCl$_3$, δ): 1.12 (s), 1.41 (s), 2.06 (m) and 3.30 (m) ppm; $^{13}$C NMR (CDCl$_3$, δ): 25.4, 28.3, 28.8, 43.8, 44.2, 80.8 and 176.2 ppm; MS (TOF) ESI+: [M+Na]$^+$, 273.04, 275.03 Da.

Synthesis of tert-butyl 2-(2-bromoethyl)hexanoate (1vii)

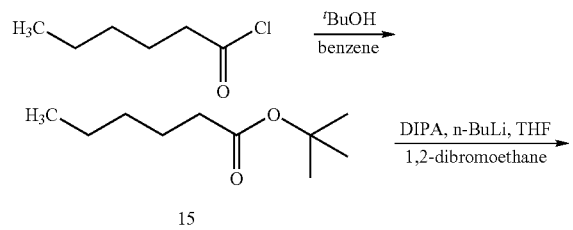

Hexanoyl chloride (160 mL, 1.16 mol) was quickly added to t-butanol (626 g, 8.44 mol) at room temperature, under argon, while stirring. The reaction temperature initially dropped, but then began to rise as the addition of hexanoyl chloride proceeded. The reaction vessel was then placed on a room-temperature water bath to maintain the temperature at approximately 25 to 35° C. After the addition was complete, the water bath was removed, and the reaction mixture was stirred for an additional 2 hours at ambient temperature. The reaction mixture was then poured into a mixture of hexane and ice water. The organic layer was separated, washed with a solution comprising 10% aqueous Na$_2$CO$_3$ and 10% NaOH (1:1), washed twice with brine, and dried over sodium sulfate. The dried organic layer was concentrated to dryness to afford 15 as a clear oil (173 g, 86.5% yield) that was used without further purification.

n-Butyllithium (2.5 M in hexanes, 106 mL, 265 mmol) was added dropwise to a solution of diisopropylamine (37 mL, 264 mmol) in THF (0.8 L) over a period of 30 minutes, at −78° C., and under argon. The mixture was stirred for an additional 20 minutes at −78° C., and compound 15 (39 g, 226 mmol) was added. The mixture was allowed to warm to −20° C. for 30 minutes before 1,2-dibromoethane (47 mL, 545 mmol) was added to the mixture in one portion. After addition of the 1,2-dibromoethane, the reaction mixture was allowed to warm to 0° C. for 1.5 hours, and was then poured into a mixture of tert-butyl methyl ether (2 L) and ice cold aqueous NaHSO$_4$ (1 M, 400 mL). The organic layer was separated, washed with a solution of aqueous NaHSO$_4$ (1 M, 100 mL) and water (300 mL), and then washed multiple times with saturated aqueous NaHCO$_3$ until the pH of the aqueous layer was 8 to 9. The organic layer was then washed with brine, dried over sodium sulfate, and concentrated to dryness to give crude 1vii. The crude product was distilled under high vacuum (1 mm Hg) and a fraction was collected at approximately 88° C. to 105° C. The product (13.5 g) was further purified by flash chromatography (silica gel) using dichloromethane/hexane 1:1 as the eluent. Appropriate fractions were combined and concentrated to afford pure compound 1vii as a clear oil (8.2 g, 13% yield). $^1$H NMR (CDCl$_3$, δ): 0.88 (t), 1.29 (m), 1.45 (m), 1.45 (s), 1.59 (m), 1.91 (m,), 2.15 (m), 2.45 (m), 3.35 (m) and 3.40 (m) ppm; $^{13}$C NMR (CDCl$_3$, δ): 13.9, 22.5, 28.1, 29.2, 31.1, 31.8, 35.2, 44.9, 80.5 and 174.5 ppm; MS (TOF) ESI+: [M+Na]$^+$, 301.12, 303.12 Da.

Synthesis of tert-butyl 2-(bromomethyl)hexanoate (1xiv)

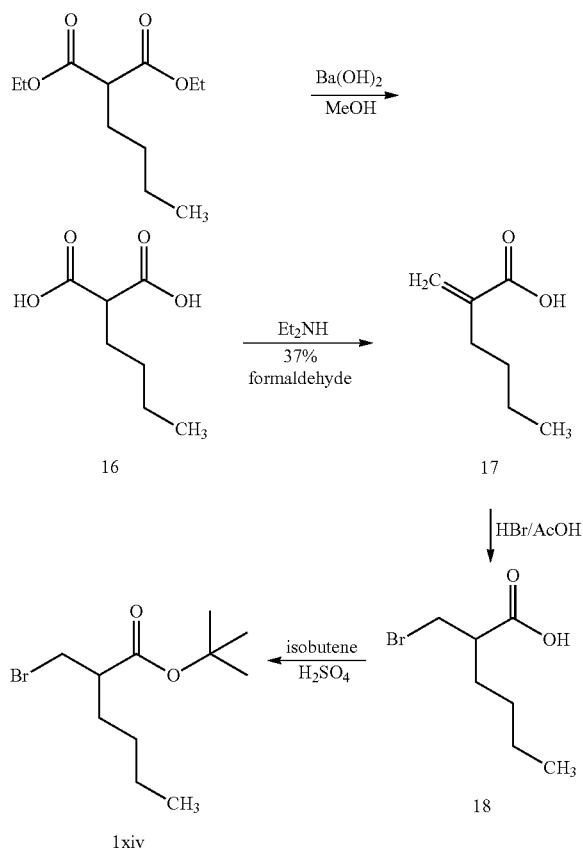

Barium hydroxide (32.8 g, 191 mmol) in methanol (150 mL) was added to a solution of diethyl butylmalonate in methanol (150 mL) while stirring. After 10 minutes, the reaction mixture became a thick suspension and stirring ceased. The reaction mixture was allowed to stand at room temperature for 3 hours, and was then concentrated to a small volume under reduced pressure. The resulting residue was suspended in tert-butyl methyl ether, and the solid was collected by filtration. The collected solid was suspended in a mixture of tert-butyl methyl ether (400 mL) and 1 M HCl (400 mL) and stirred for 3 hours. The organic layer was separated and the aqueous layer was extracted with tert-butyl methyl ether. The tert-butyl methyl ether layers were pooled, and the combined layer was washed with brine, dried over sodium sulfate and concentrated to dryness to provide 16 as a white solid (18 g, 78% yield) that was used without further purification.

A mixture of 16 (155 g, 0.969 mol), 37% formaldehyde (300 mL, 4.03 mol) and diethylamine (190 mL, 1.83 mol) was stirred at ambient temperature for about 10 minutes, refluxed for 2 hours, and then cooled to ambient temperature. The reaction mixture was concentrated to a small volume under reduced pressure. The residue was partitioned between tert-butyl methyl ether and 1 M HCl. The organic layer was separated, washed with brine, dried over sodium sulfate and concentrated to dryness to afford 17 as a clear oil (103.4 g, 83% yield).

A mixture of 17 (103.4 g, 0.815 mol) and HBr (31% in acetic acid, 0.4 L, 2.14 mol) was stirred at ambient temperature overnight. The reaction mixture was poured into a mixture of tert-butyl methyl ether and ice water. The organic layer was separated, washed with 1 M HCl, washed with brine and then dried over sodium sulfate. The dried organic layer was concentrated to dryness to afford compound 18 as a yellow oil (157 g, 92% yield).

A mixture of 18 (27 g, 0.129 mol) and 95% sulfuric acid (3.2 g, 0.031 mol) was stirred in a lyophilizing vessel that had been placed in a stainless steel pressure vessel. The lyophilizing vessel served as a glass liner. The assembly was maintained at approximately −50° C. Isobutene (45 g, 0.804 mol) was added, and the pressure vessel was sealed and allowed to reach ambient temperature. Stirring was continued at ambient temperature for 2 days. After that time, the pressure was carefully released, and the reaction mixture was diluted with tert-butyl methyl ether. The organic layer was separated and washed multiple times with ice cold aqueous sodium bicarbonate until the pH of the aqueous layer was 8 to 9. The organic layer was then washed with brine, dried over sodium sulfate and concentrated to dryness. The resulting residue was applied to a silica gel column and eluted with dichloromethane (0 to 25%) in hexane. Appropriate fractions were combined and concentrated to afford pure compound 1xiv as a clear oil (18 g, 52% yield). $^1$H NMR (CDCl$_3$, δ): 0.94 (t), 1.35 (m), 1.52 (s), 1.60 (m), 1.68 (m), 2.70 (m), 3.45 (m) and 3.56 (m) ppm; $^{13}$C NMR (CDCl$_3$, δ): 13.9, 22.5, 28.1, 29.0, 31.0, 33.1, 48.9, 81.1 and 172.4 ppm; MS (TOF) ESI+: [M+Na]$^+$, 287.08, 289.09 Da.

Example 2

Syntheses of Scheme 2 Intermediates

Synthesis of tert-Butyl 4-(2-(2-hydroxyethoxy)ethoxy)-2,2-dimethylbutanoate (6ii)

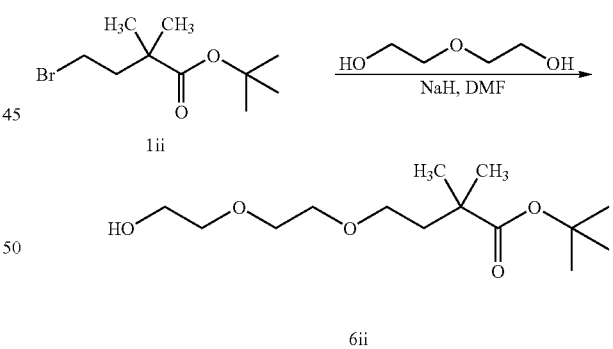

The following procedure was performed under argon. A mixture of diethylene glycol (18 mL, 0.19 mol) and toluene (50 mL) was dried by azeotropic distillation using a Dean-Stark condenser. The residue was cooled to room temperature and anhydrous DMF (40 mL) was added. The solution was then cooled to 0° C. using an ice bath and NaH (60% dispersion in mineral oil, 823 mg, 21 mmol) was added. After 5 minutes, the ice bath was removed and the mixture was allowed to warm to room temperature. After 1 hour and 50 minutes, t-butyl 4-bromo-2,2-dimethylbutyrate (3.046 g, 12.1 mmol), 1ii, was added to the mixture with DMF (2 mL). The reaction was stirred at room temperature overnight. The reaction mixture was then added to water and extracted with dichloromethane. The combined organic extracts were washed with water, washed with brine, dried over Na$_2$SO$_4$, filtered, and concentrated in vacuo. Silica gel column chromatography (ethyl acetate/hexanes 1:4 to 4:1) afforded 6ii as a clear oil (240 mg, 7.2% yield) that was pure by TLC. An additional 142 mg (clear oil) of material was obtained, but it included an impurity that was visualized as a spot of higher R$_f$ by TLC. $^1$H NMR (CDCl$_3$, δ): 1.13 (s), 1.41 (s), 1.81 (t), 2.62 (br. s), 3.47 (t), 3.55 (m), 3.58 (m), 3.62 (m) and 3.70 (m) ppm; $^{13}$C NMR (CDCl$_3$, δ): 25.6, 28.1, 39.8, 41.4, 61.9, 68.4, 70.3, 70.5, 72.6, 80.1 and 177.0 ppm; ESI(+) MS: [M+Na]$^+$=299.16; [M+K]$^+$=315.17 daltons.

Synthesis of
2-(2-methoxypolyethoxy)ethyl)hexanoic acid (8vii)

A solution of mPEG-OMs (about 5000 Da, 4.1 g, 0.82 mmol) in toluene (110 mL) was dried by azeotropic distillation using a Dean-Stark trap, and a 70-mL portion of the toluene was removed. In another flask, Compound 6vii (2.5 g, 8.23 mmol) was dissolved in toluene (100 mL), the mixture was dried by azeotropic distillation, and a 60-mL portion of toluene was removed. The resulting residue was cooled to 0° C. and NaH (500 mg, 12.4 mmol) was added to form a mixture. This mixture was stirred at 0° C. for 0.5 hours. The dried solution of mPEG-OMs was added to the mixture at room temperature and the mixture was refluxed overnight. The reaction was then cooled to room temperature, concentrated to a residue, and redissolved in a minimum amount of dichloromethane (DCM). TBME was added to the solution and the resulting precipitate was collected by filtration. The precipitate was dissolved in dichloromethane (200 mL), washed with water, and then with brine. The solution was

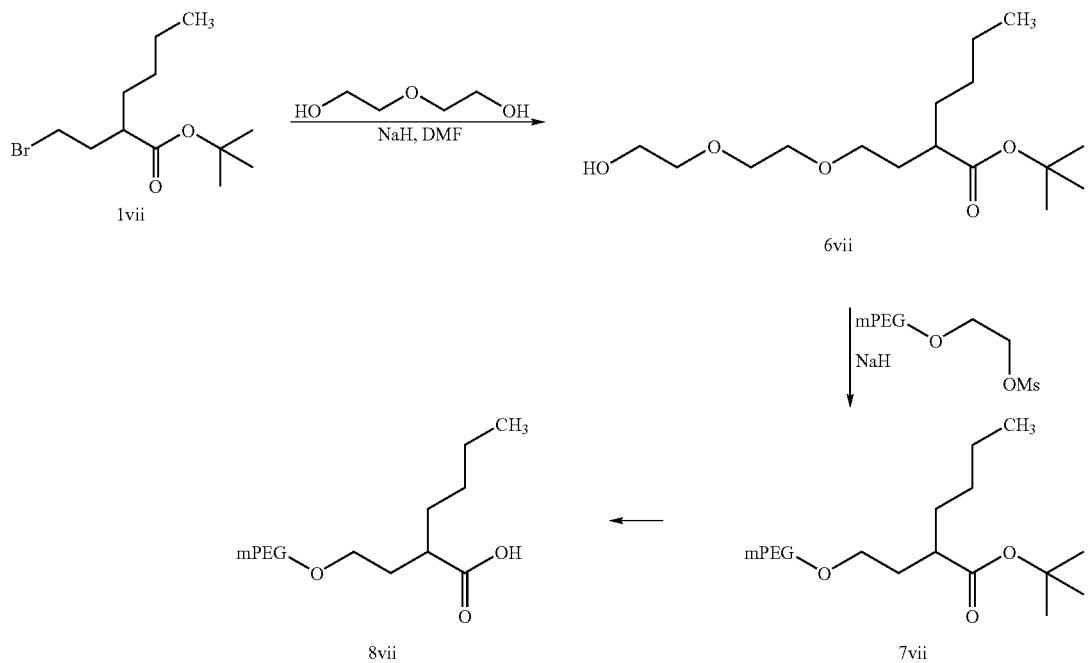

A mixture of diethylene glycol (33 g, 0.32 mol) and toluene (120 mL) was dried by azeotropic distillation using a Dean-Stark condenser and the resulting residue was cooled to room temperature. Anhydrous dimethylformamide (DMF, 50 mL) was added to the residue and the mixture was cooled to 0° C. Sodium hydride (NaH, 1080 mg, 60% in mineral oil, 27 mmol), was then added and the mixture was stirred for 1 hour. Compound 1vii (5.0 g, 18 mmol) was added and the mixture was stirred at room temperature overnight. The reaction mixture was then poured into water and extracted with dichloromethane. The organic layer was washed with brine, dried over Na$_2$SO$_4$ and concentrated to dryness. The resulting residue was applied to a flash chromatography column (silica gel) and eluted with methanol (5% to 10%) in dichloromethane. Appropriate fractions were pooled and concentrated to yield compound 6vii as a clear oil (3.0 g, yield 55%). $^1$H NMR (CDCl$_3$, δ): 0.82 (m), 1.22 (m), 1.38 (s), 1.38 (m, unresolved), 1.52 (m), 1.63 (m), 1.81 (m), 2.29 (m), 3.41 (m), 3.53 (m), 3.59 (m) and 3.66 (m) ppm; $^{13}$C NMR (CDCl$_3$): 14.0, 22.6, 28.2, 29.4, 32.3, 32.4, 43.4, 61.8, 69.4, 70.3, 70.4, 72.6, 80.1, and 175.4 ppm; MS (TOF) ESI+: [M+Na]$^+$, 327.19 Da.

dried over Na$_2$SO$_4$ and concentrated. TBME was added to the residue to afford the product 7vii as a light yellow solid (3.6 g, about 82% yield, see e.g. International Publication No. WO 2006/099794). TLC (MeOH/CHCl$_3$/NH$_4$OH 10/90/1) indicated the presence of the 7vii, along with a small amount of impurities. Compound 7vii was used in the next step without further purification.

Compound 7vii (3.6 g) was dissolved in DCM/trifluoroacetic acid (20 mL, 1:1), and the solution was stirred at room temperature overnight. The reaction mixture was concentrated, and the resulting residue was redissolved in DCM, washed with water, and then washed with brine. The solution was dried over sodium sulfate, concentrated to small volume and diluted with TBME. The precipitate was collected by filtration and purified by flash chromatography (silica gel), eluting with methanol (7% to 10%) in DCM containing 1 to 2% NH$_4$OH. Appropriate fractions were pooled and concentrated to afford pure 8vii (1.6 g, 31% yield for the last two steps.

Example 3

Synthesis of 4-(Hydroxymethyl)phenyl 2-(2-methoxypolyethoxy)ethyl)hexanoate (10vii)

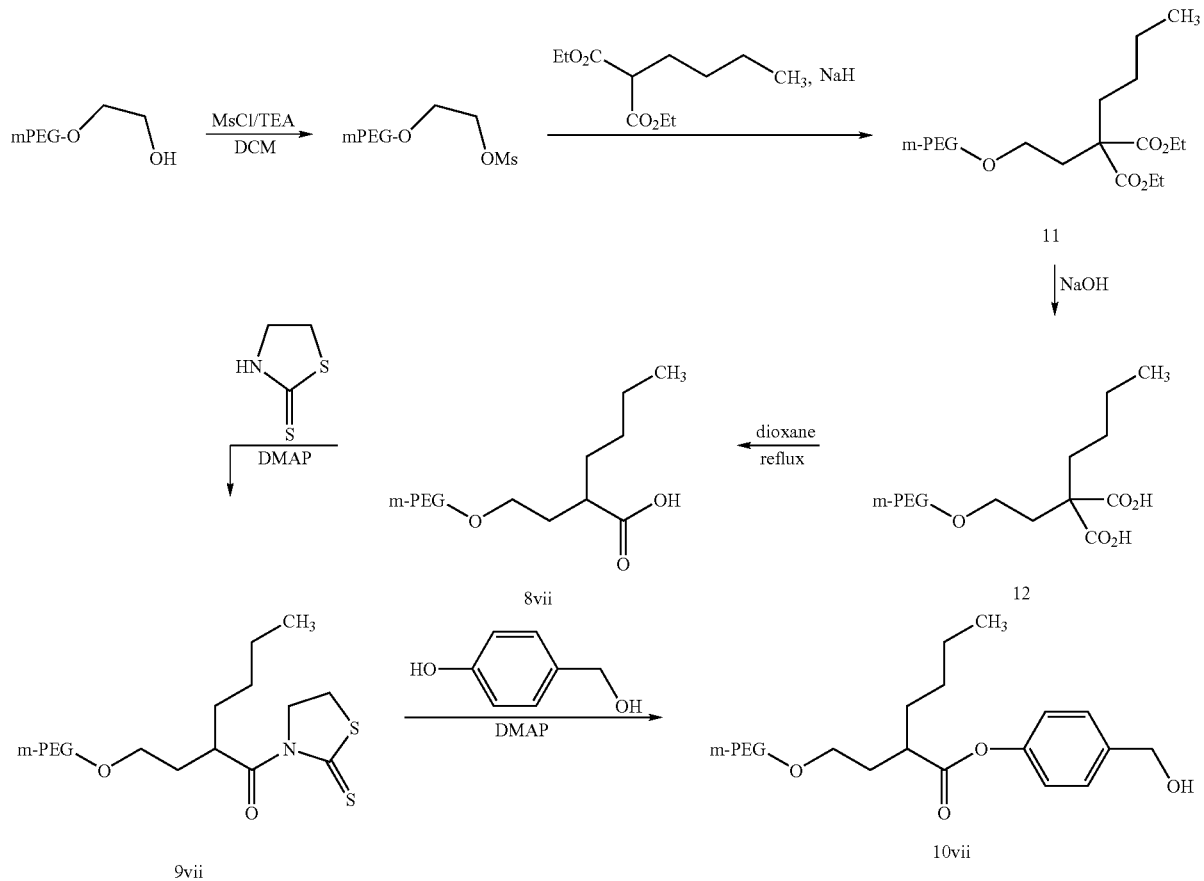

Step 1: Preparation of mPEG(5000) methanesulfonate (mPEG-OMs)

Monomethoxy poly(ethylene glycol) methanesulfonate (about 5000 Da) was prepared as described in International Publication No. WO 2004/063250, which is incorporated herein by reference. Specifically, mPEG-OH (about 5000 daltons, 30 grams) was reacted with methanesulfonyl chloride (MsCl, 4.3 equivalents) and triethylamine (TEA, 4.8 equivalents) in dichloromethane/toluene to yield 30 grams of mPEG-OMs.

Step 2: Preparation of mPEG(5000)-CH$_2$CH$_2$C(n-C$_4$H$_9$)(CO$_2$Et)$_2$ (11)

The compound, mPEG-OMs, was treated with diethyl butylmalonate (40 equivalents) and NaH (40 equivalents) in toluene/1,4-dioxane (1:1, 800 mL) according to the method described in International Publication No. WO 2004/063250, modified by a greater excess of malonate and NaH to force the reaction to completion. The reaction mixture was refluxed overnight and then concentrated to a small volume. Dichloromethane and ice water were added to the reaction mixture to result in a biphasic system. The aqueous layer was adjusted to pH 1.0 with concentrated HCl, the layers were shaken, and the organic layer was separated, dried over sodium sulfate and concentrated to a small volume. t-Butyl methyl ether was added to the organic layer and the resulting precipitate was collected by filtration to afford mPEG(5000)-CH$_2$CH$_2$C(n-C$_4$H$_9$)(CO$_2$Et)$_2$ (11, 40 g).

Step 3: Preparation of mPEG(5000)-CH$_2$CH$_2$C(n-C$_4$H$_9$)(CO$_2$H)$_2$ (12)

Compound 11 was combined with an aqueous solution of NaOH (8.1 g) and NaCl (1.3 g) in water (100 mL), and heated at 80° C. overnight. The solution was then cooled to ambient temperature, dichloromethane was added to form a biphasic system, and the aqueous layer was adjusted to pH 1.8 to 2.0 with concentrated HCl. The layers of the biphasic system were shaken, and the organic layer was separated. The aqueous layer was back-extracted with dichloromethane, and the organic layers were pooled, dried over sodium sulfate, and concentrated to a small volume. t-Butyl methyl ether was added to the small volume of the organic layer, and the resulting precipitate was collected by filtration to afford 12 (29 g) as a white solid.

Step 4: Preparation of mPEG(5000)-CH$_2$CH$_2$C(n-C$_4$H$_9$)(CO$_2$H) (8vii)

Compound 12 (29 g) in dioxane (150 mL) was treated as described in International Publication No. WO 2004/063250. The reaction mixture was refluxed overnight, cooled to room temperature and concentrated to dryness. The resulting residue was dissolved in a small amount of dichloromethane, t-butyl methyl ether was added, and the resulting precipitate was collected by filtration to afford 8vii (27.4 g) as a white solid. TLC analysis was performed on an activated silica gel plate using $CHCl_3$:MeOH:$NH_4OH$ (90:10:1) as the developing solvent. Compound 8vii appeared as an essentially pure compound ($R_f$ approximately 0.45) with very slight contamination from a component of higher $R_f$ (approximately 0.50) that co-eluted with mPEG-OH.

Step 5: Preparation of mPEG(5000)-$CH_2CH_2$C(n-$C_4H_9$)(C(=O)tz), (9vii) (tz=thiazolidine-2-thione-3-yl)

Compound 8vii (2.0 g 0.4 mmol), dimethylaminopyridine (DMAP, 98 mg, 0.8 mmol) and 2-mercaptothiazoline (95 mg, 0.8 mmol) were dissolved in anhydrous dichloromethane (5 mL), and the solution was cooled to 0° C. After stirring for 15 minutes, 1-ethyl-3-(3-dimethylaminopropyl)carbodiimide hydrochloride (EDC-HCl, 153 mg, 0.8 mmol) was added. Stirring was continued at 0° C. to room temperature overnight. TLC (90:10:1 $CHCl_3$:MeOH:$NH_4OH$) showed complete consumption of mPEG(5000)-$CH_2CH_2$C(n-$C_4H_9$)($CO_2H$) from Step 4. t-Butyl methyl ether was added to the crude product, and the resulting precipitate was collected by filtration and dried to afford 9vii as a yellow solid (2 g).

Step 6: Preparation of 4-(Hydroxymethyl)phenyl 2-(2-(2-methoxypolyethoxy)ethyl)-hexanoate, (10vii)

Compound 9vii (1.0 g, 0.2 mmol), 4-hydroxybenzyl alcohol (98 mg, 0.8 mmol) and DMAP (98 mg, 0.8 mmol) were dissolved in anhydrous dichloromethane (10 mL) and refluxed for 24 hours. The reaction mixture was cooled to room temperature, t-butyl methyl ether was added to it, and the resulting precipitate was collected by filtration. The precipitate was dissolved in dichloromethane, the solution was washed with 0.5 N HCl, and then with brine. The organic layer was dried over sodium sulfate and concentrated to dryness to yield a white solid. The solid was further purified by flash chromatography (silica gel), eluting with $CHCl_3$:MeOH:$NH_4OH$ (95:5:0.5 to 90:10:1). Appropriate fractions were pooled and concentrated to afford 10vii (600 mg) as a white solid. Trace DMAP was apparent in the $^1$H NMR spectrum. $^1$H-NMR (DMSO-$d_6$, δ): 0.91 (m), 1.35 (m), 1.60 (m), 1.68 (m), 1.78 (m), 1.94 (m), 2.67 (m), 3.32 (s), 3.41 (m), 3.52 (m), 4.51 (d), 5.21 (t), 7.04 (d) and 7.36 (d) ppm; $^{13}$C-NMR (DMSO-$d_6$, δ): 13.8, 22.0, 28.9, 31.5, 31.8, 42.1, 58.0, 62.3, 68.3, 69.6-70.0 (multiple unresolved signals), 71.2, 121.2, 127.4, 140.0, 149.1 and 174.1 ppm.

Example 4

Synthesis of 4-(((2,5-dioxopyrrolidin-1-yloxy)carbonyloxy)-methyl)phenyl 4-(2-methoxypolyethoxy)-2-methylbutanoate (IAi)

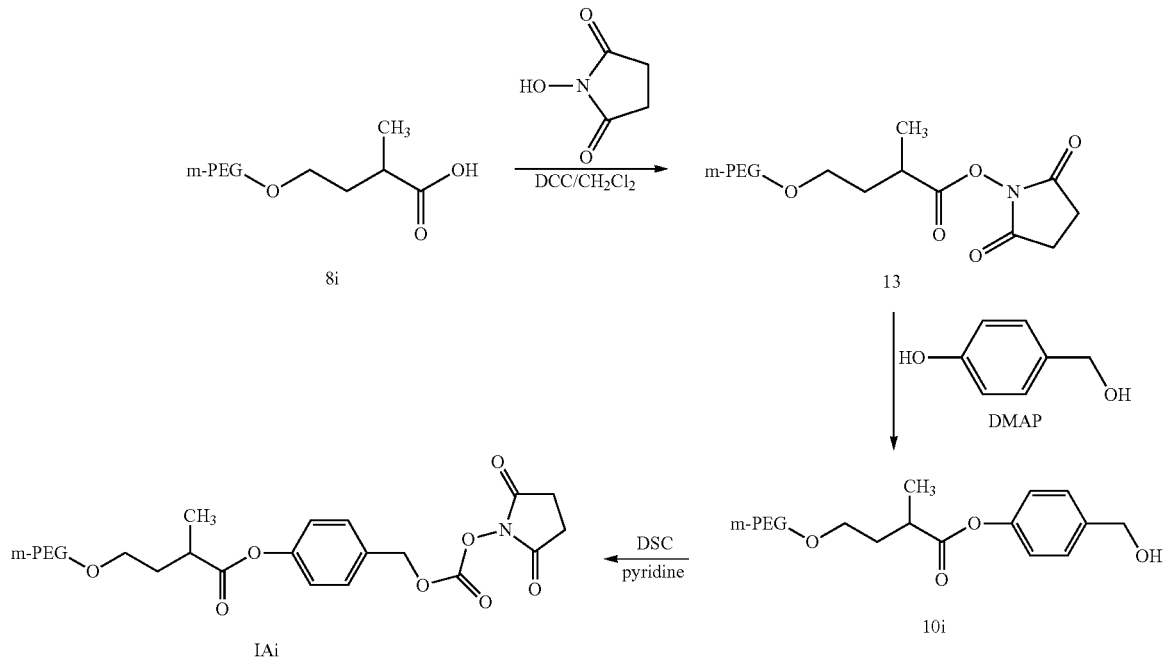

Step 1: Synthesis of 2,5-dioxopyrrolidin-1-yl 4-(2-methoxypolyethoxy)-2-methylbutanoate (13)

Compounds 8i and 13 were prepared by modifications of methods reported in U.S. Pat. No. 6,992,168. Specifically, compound 8i was obtained only by crystallization in the patent, but was further purified by flash chromatography (silica gel) using $CHCl_3$:MeOH:$NH_4OH$ (95:5:0.5 and 90:10:1) as the eluant in the instant invention. Appropriate fractions were pooled and concentrated to afford pure 8i.

Compound 8i (6.0 g, 1.2 mmol) was dissolved in 60 mL of methylene chloride. N-hydroxysuccinimide (NHS, 180 mg, 1.6 mmol) and N,N-dicyclohexylcarbodiimide (DCC, 330 mg, 1.60 mmol) in 1.6 mL of methylene chloride were added to the solution. After stirring the mixture overnight, it was filtered and the product was crystallized by addition of ethyl ether (280 mL). The mixture was cooled at 0 to 5° C. for 2 hours, the precipitate was collected by filtration, and dried under vacuum at 40° C. for 3 hours to provide compound 13 (5.58 g, 93% yield) as a white powder. $^1$H-NMR (CDCl$_3$, δ): 1.31 (d), 1.79 (m), 2.05 (m), 2.80 (s), 2.97 (m), 3.40 (s), and 3.51 (br m) ppm; $^{13}$C-NMR (CDCl$_3$, δ): 17.34, 25.95, 33.80, 34.40, 59.35, 68.40-72.31 (PEG), 169.42 and 172.05 ppm.

Step 2: Synthesis of 4-(hydroxymethyl)phenyl 4-(2-methoxypolyethoxy)-2-methylbutanoate (10i)

The conversion of 13 to 10i was performed by modification of a procedure reported in Greenwald, et. al., *J. Med. Chem.*, 1999, 42(18), 3657-3667, which is incorporated herein by reference in its entirety. To a solution of 13 (5.5 g, 1.1 mmol) in 55 mL of methylene chloride, dimethylaminopyridine (DMAP, 550 mg, 4.4 mmol) and 4-hydroxybenzyl alcohol (550 mg, 4.4 mmol) were added. The mixture was refluxed for 24 hours, cooled to room temperature, stirred for an additional 40 hours, and filtered. The filtrate was evaporated to dryness and the resulting residue was dissolved in hot 2-propanol (100 mL). The solution was cooled to 0 to 5° C. for 3 hours and a precipitate formed. The precipitate was collected by filtration, washed with 2-propanol (30 mL) and ethyl ether (50 mL), and dried under vacuum at 45° C. for 2.5 hours to provide 10i (4.93 g, 90%) as a white solid. Maldi TOF mass spectra were obtained for both 13 and 10i. The theoretical and observed mass differences were compared for the same homologue as previously described. Thus, for homologue 105, the observed masses for 13 and 10i were 4890.0 and 4899.2 daltons, respectively. The observed difference is 9.2 daltons. The theoretical difference for the non-repeating units is an increase of 9.03 daltons. Thus, the mass spectral data support the claim that the expected reaction has occurred. $^1$H-NMR (CDCl$_3$, δ): 1.35 (d), 1.84 (m), 2.15 (m), 2.89 (m), 3.35 (s), 3.51 (br m), 4.71 (s), 7.10 (d) and 7.42 (d) ppm; $^{13}$C-NMR (CDCl$_3$, δ): 17.12, 33.44, 36.79, 59.06, 68.84-72.00 (PEG), 121.60, 127.98, 138.64, 150.21 and 175.00 ppm.

Step 3: Synthesis of 4-(((2,5-dioxopyrrolidin-1-yloxy)cabonyloxy)-methyl)phenyl 4-(2-methoxy-polyethoxy)-2-methylbutanoate (IAi, MW about 5000 daltons)

Compound 10i was converted to IAi by a modification of the method of Greenwald et al. To a solution of 10i (1.25 g, 0.25 mmol) in 20 mL of methylene chloride was added disuccinimidyl carbonate (DSC, 128 mg, 0.5 mmol) and pyridine (79 mg, 1.0 mmol). The mixture was stirred for 18 hours at room temperature to form a clear solution. The solution was evaporated to dryness, and the residue was dissolved in methylene chloride (60 mL). The methylene chloride solution was washed sequentially with aqueous HCl (0.1 N, 20 mL), saturated NaHCO$_3$ (25 mL), and saturated NaCl (25 mL). The organic layer was dried with Na$_2$SO$_4$ and evaporated to dryness. The residue was dissolved in methylene chloride (10 mL), and ethyl ether (40 mL) was added. The mixture was cooled to 0 to 5° C. for 2 hours. The resulting precipitate was collected by filtration, washed with ethyl ether (40 mL) and dried under vacuum at 40° C. for 2 hours to provide IAi (890 mg, 71%) as a white solid. $^1$H-NMR (CDCl$_3$, δ): 1.36 (d), 1.84 (m), 2.15 (m), 2.87 (s), 2.89 (m, unresolved), 3.47 (s), 3.51 (br m), 5.33 (s), 7.14 (d) and 7.44 (d) ppm; $^{13}$C-NMR (CDCl$_3$, δ): 17.01, 25.49, 33.39, 36.79, 59.06, 68.80-72.15 (PEG), 122.06, 129.91, 130.68, 138.64, 151.59, 168.55 and 174.74 ppm.

Example 5

Synthesis of 4-(((2,5-dioxopyrrolidin-1-yloxy)carbonyloxy)-methyl)phenyl 4-(2-methoxypolyethoxy)-2-methylbutanoate (IAi, Scheme 4, MW about 2000 daltons)

Step 1: Synthesis of 4-(hydroxymethyl)phenyl 4-(2-methoxypolyethoxy)-2-methylbutanoate (10i)

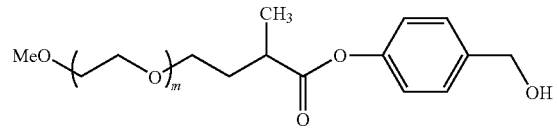 [SMILES: COCCOCCC(C)C(=O)Oc1ccc(CO)cc1]

To 4-hydroxybenzyl alcohol (1.1235 g, 9.05 mmol, 12 eq) in a 200-mL pear-shaped flask was added 30 mL of acetonitrile. The vessel was stoppered and the mixture was stirred vigorously at room temperature until most of the alcohol dissolved. Triethylamine (1.270 mL, 9.07 mmol, 12 eq) was added to the vessel and a white precipitate formed. The mixture was stirred for an additional 30 min, and 13 from scheme 4 (1.5066 g, 0.7533 mmol, 1 equivalent) was added. Compound 13 is a derivative of mPEG(MW about 2000 Da), wherein m is approximately 40. Stirring was continued at room temperature, and the reaction was monitored by TLC. After 42 hours, the mixture appeared as a cloudy gray/white suspension. Nearly all of the starting material had been consumed. The mixture was concentrated under high vacuum to a tan oil and methylene chloride (30 mL) was added. The resulting mixture was stirred vigorously for 45 minutes, forming a light tan slurry. The slurry was allowed to stand for 2 hours, whereupon it was transferred to two screw-top TEFLON® centrifuge tubes. The reaction vessel was rinsed with two 6-mL portions of methylene chloride, and a single rinsing was transferred to each of the two centrifuge tubes. Finally, the reaction vessel was rinsed with two 10-mL portions of ice cold water to dissolve any remaining solid material, and a single rinsing was transferred to each of the two centrifuge tubes. The tubes were shaken intermittently, with venting, for 30 sec, and were then centrifuged. The aqueous layer (top) was removed from each tube. This water extraction removed unreacted 4-hydroxybenzyl alcohol and triethylammonium salts. The extraction with ice cold water was repeated in the same manner five additional times with each of the two tubes.

The organic layers were combined and observed to be cloudy. This cloudy solution was brought to 110 mL with methylene chloride and filtered through a sintered glass funnel (fine). The filtrate, still somewhat cloudy, was concentrated by rotary evaporation under high vacuum using a 24° C. water bath to yield a white semi-solid. Ethyl ether (50 mL) was added, and the mixture was stirred vigorously for 2 hours, thus converting the product to a suspension of a white granular solid. The suspension was filtered through a medium porosity sintered glass funnel, and the precipitate was dried under high vacuum at 24° C. for 12 h to yield 10i as a white solid, 1.15 g (about 80% yield). $^1$H-NMR (CDCl$_3$, δ): 1.31 (d), 1.80 (m), 2.12 (m), 2.84 (m), 3.37 (s), 3.54 (m), 3.63, 4.67 (s), 7.05 (d) and 7.37 (d) ppm.

Mass spectrometry was used to verify that the molecular weight difference between compounds 13 and 10i was as expected. These spectra consisted of a well-resolved envelope of peaks due to the homologues of the polymer. Each homologue was 44 daltons apart, as expected. For a given homologue, the total mass of the repeating ethylene oxide units (—CH$_2$CH$_2$O—) is the same in both molecules. Therefore, the mass difference would be due to the difference in the non-repeating end group units. The exact masses of the non-repeating end group units for 13 and 10i are 229.10 daltons and 238.12 daltons, respectively, and the difference in molecular weight between the starting material and the product is an increase of 9.02 daltons. The homologue due to 42 repeating units was identified for both 13 and 10i. The observed masses were 2101.50 daltons and 2110.12 daltons for 13 and 10i, respectively, and the difference was an increase of 8.62 daltons. This value compared favorably to the expected difference of 9.02 daltons, and therefore, the mass spectral data supports the claim that the expected reaction has occurred. The number of repeating units in a particular homologue was determined by subtracting the total mass of the non-repeating units, including sodium, from the observed mass and dividing the remainder by the mass of ethylene oxide, 44.03 daltons. Integer values were obtained. The integers were the number of repeating units in the homologue.

Step 2: Synthesis of 4-(((2,5-dioxopyrrolidin-1-yloxy)carbonyloxy)-methyl)phenyl 4-(2-methoxy-polyethoxy)-2-methylbutanoate (IAi)

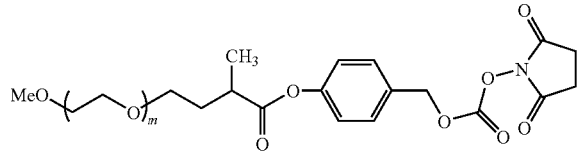 [SMILES: COCCOCCC(C)C(=O)Oc1ccc(COC(=O)ON2C(=O)CCC2=O)cc1]

Compound IAi was prepared by adapting the method of Ghosh et al. (Tetrahedron Lett. 33, 2781-2784 (1992)). Compound 10i (1.0012 g, 0.500 mmol, 1 eq) was added to 15 mL of acetonitrile and stirred under argon. N,N'-Disuccinimidyl carbonate (DSC) (0.2582 g, 1.01 mmol, 2 eq) was added to the solution, followed by an additional 5 mL of acetonitrile. Triethylamine (282 µL, 2.02 mmol, 4 eq) was added to the rapidly stirring solution and stirring was continued for 4 hours. At that time the mixture appeared turbid and gray/white, and TLC evaluation indicated that 10i had been completely converted to IAi. The somewhat cloudy solution was concentrated to dryness by rotary evaporation under high vacuum using a 24° C. water bath. The semi-solid residue (slightly yellow) was dissolved in methylene chloride, 40 mL, and distributed between two screw-top TEFLON® centrifuge tubes. The solution in each tube was extracted with 10 mL of aqueous sodium bicarbonate, pH 8.26, by shaking the tube vigorously for 30 seconds, centrifuging the emulsion, and removing the aqueous layer. The extraction was repeated three additional times. The resulting organic layer in each tube was washed with 10 mL of water four times and centrifuging was used to break the emulsion. The organic layers were combined and concentrated to a white semi-solid residue. Ethyl ether (50 mL) was added to the residue, and the mixture was stirred vigorously for 5 hours at room temperature to convert the semi solid to a white granular solid. The resulting suspension was filtered through a sintered glass funnel (medium) and dried under high vacuum at 24° C. for four hours to yield a crude sample of IAi (0.895 g, about 89% yield), which contained only minor impurities by TLC and NMR. A portion of compound IAi (0.3198 g) was recrystallized by dissolving it in 12.5 mL of chloroform and then adding ethyl ether (42 mL). The solution was refrigerated overnight. The resulting white granular precipitate was collected by filtration through a sintered glass funnel (medium) to yield 0.23 g of recrystallized product. This product was recrystallized a second time using 8 mL of chloroform and 27 mL of ethyl ether. The resulting precipitate was dried under high vacuum at 24° C. for 10 hours to constant weight, yielding 0.16 g of purified IAi. $^1$H-NMR (CDCl$_3$, δ): 1.28 (d), 1.77 (m), 2.08 (m), 2.80 (s), 2.83 (m, unresolved), 3.34 (s), 3.51 (m), 3.60, 5.26 (s), 7.08 (d) and 7.38 (d) ppm.

Mass spectrometry was used to verify that the molecular weight difference between 10i and IAi was as expected. As in the case of the mass difference between 13 and 10i, the mass difference between equivalent homologues of 10i and IAi should depend on the difference between the non-repeating end group units. The exact masses of the non-repeating units for 10i and IAi are 238.12 daltons and 379.13 daltons, respectively, and the difference in molecular weight between intermediate 10i and product IAi is an increase of 141.01 daltons. The homologue due to 42 repeating units was identified for both 10i and IAi. The observed masses were 2110.12 daltons and 2251.38 daltons for 10i and IAi, respectively, and the difference was an increase of 141.26 daltons. This value compared favorably to the expected difference of 141.01 daltons, and therefore, the mass spectral data supports the claim that the expected reaction has occurred. The number of repeating units in a particular homologue was determined in the same manner as for 10i, above. The fact that integers were obtained for this calculation supported the claim that the assumed weight of the non-repeating units was correct.

Example 6

Preparation of PEGylated Tryptophan

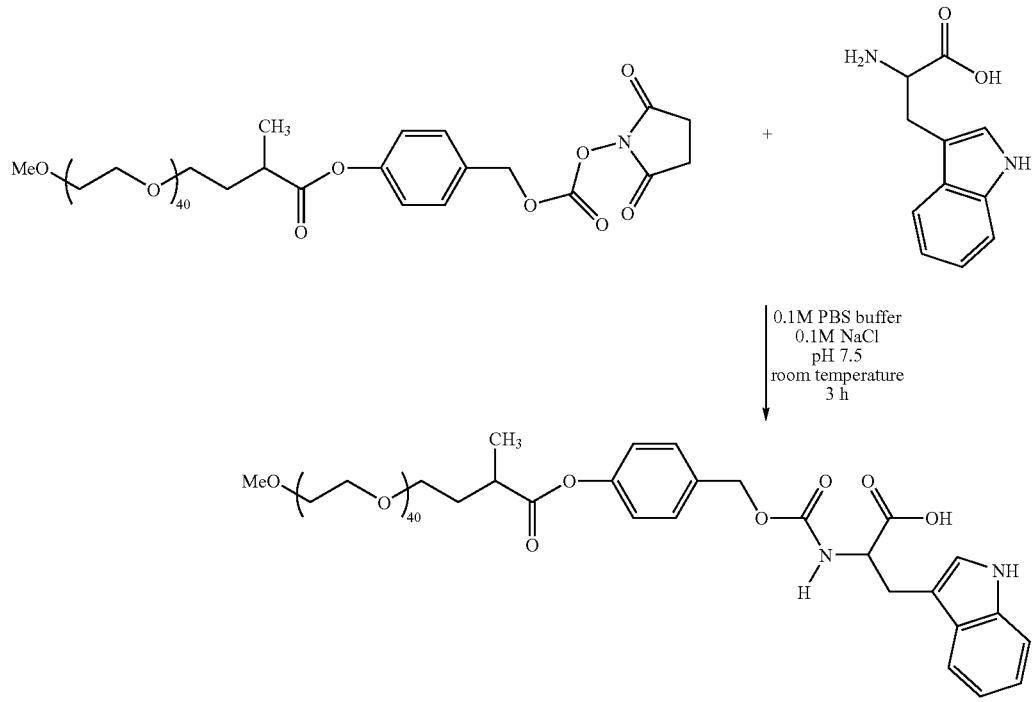

Tryptophan (1.7 mg, 8.3 µM) was dissolved in 1 mL of PBS buffer (0.10 M, NaCl 0.10 M, pH 7.5) and stirred. To the stirring solution was added 28.5 mg of the PEG derivative IAi (MW about 2300, about 12.4 µM), and the mixture was allowed to stir at room temperature for 60 minutes. Additional PEG derivative (7.5 mg) was added to 0.7 mL of this reaction mixture and further stirred at room temperature for another two hours. A 0.10 mL aliquot of the reaction mixture was mixed with 8 µL of HCl (1.0 N) and diluted to about 1 mL using 20% acetonitrile containing 0.01% trifluoroacetic acid. A 0.050 mL aliquot of the resulting solution was used for HPLC analysis (Example 8).

Example 7

Release of Tryptophan from PEG-Tryptophan

A 0.10 mL aliquot of the PEGylated tryptophan reaction solution from Example 7 was diluted with 0.60 mL PBS buffer (0.10 M, NaCl 0.10 M, Glycine 0.10M, pH 7.5) and incubated at 37° C. in an oven. Aliquots of 0.10 mL were withdrawn at incubation intervals of 2, 7, 32 and 102 hours, and were quenched with 10 µl of HCl (1.0 N diluted with 0.4 mL 20% acetonitrile containing 0.01% trifluoroacetic acid) for HPLC analysis (0.10 mL injection).

The above procedure was repeated using a cleavage solution with a pH of 8.5 and incubation intervals of 1, 6, 24, and 32 hours.

HPLC Analysis:

Both the PEG-tryptophan (Example 7) and cleavage samples were analyzed on C-18 reversed-phase HPLC with detection at 280 nm. The HPLC conditions are the following: C-18 column (Waters Symmetry, 4.6×250 mm), flow rate of 1.0 mL/min, gradient of acetonitrile 20% to 80% over 15 minutes followed by 10 minutes of washing at 80% acetonitrile (all contain 0.01% trifluoroacetic acid).

Results:

The contents of tryptophan and PEG-tryptophan (integration area) of cleavage reactions at pH 7.5 were analyzed on HPLC and listed below.

|  | Incubation Time (hours) | | | |
| --- | --- | --- | --- | --- |
|  | 2 | 7 | 32 | 102 |
| Tryptophan | 596 | 647 | 1329 | 2955 |
| PEG-Tryptophan | 6314 | 5538 | 5039 | 2546 |

An increase of tryptophan and decrease of PEG-tryptophan was observed over the time period of 102 hours. The half-life of PEG-tryptophan at pH 7.5 is about 85 hours.

The contents of tryptophan and PEG-tryptophan (integration area) of cleavage reactions at pH 8.5 were analyzed on HPLC and listed below.

|  | Incubation Time (hours) | | | |
| --- | --- | --- | --- | --- |
|  | 1 | 6 | 24 | 32 |
| Tryptophan | 735 | 1183 | 2442 | 2498 |
| PEG-Tryptophan | 7967 | 6235 | 2754 | 1642 |

An increase of tryptophan and decrease of PEG-tryptophan was observed over the time period of 32 hours. The half-life of PEG-tryptophan at pH 8.5 is about 17 hours.

Incubation of PEGylated tryptophan at pH 7.5 plus glycine or at pH 8.5 clearly shows the trend of increasing tryptophan and decreasing of PEGylated tryptophan. The half-life of PEGylated tryptophan was determined to be 17 hours at pH 8.5 and 85 hours at pH 7.5 in the presence of glycine. The total sum of tryptophan plus PEGylated tryptophan decreased over time, most likely due side reactions of tryptophan, the products of which are shown in the HPLC spectra.

What is claimed is:

1. A compound of Formula I:

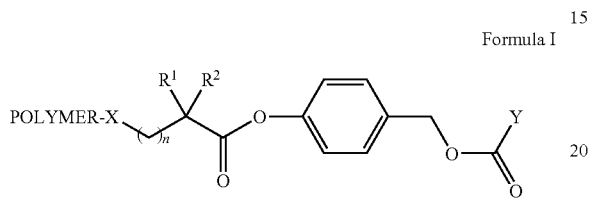

Formula I wherein Y is an activating group;
X is selected from the group consisting of O, S and $NR^3$;
n is 1, or 2;
POLYMER is a water soluble, non-peptidic polymer wherein POLYMER does not comprise a poly(alkylene glycol);
$R^1$, and $R^2$, are independently selected from the group consisting of hydrogen, $(C_1-C_6)$-alkyl, $(C_1-C_6)$-alkylenearyl, and aryl with the proviso that at least one of $R^1$, and $R^2$, is different from hydrogen; and
$R^3$, is selected from the group consisting of hydrogen, $(C_1-C_6)$-alkyl, $(C_1-C_6)$-alkylenearyl, and aryl.

2. The compound according to claim 1, wherein POLYMER is selected from the group consisting of polyvinylpyrrolidone, poloxamer, polysaccharide, polysialic acid, hydroxyethyl starch, icodextrin, chondroitin sulfate, dermatan sulfate, heparin, chitosan, hyaluronic acid, dextran, dextran sulfate, and pentosan polysulfate.

3. The compound according to claim 1, wherein $R^1$, and $R^2$, are independently selected from the group consisting of hydrogen, methyl, ethyl, n-propyl, isopropyl and n-butyl.

4. The compound according to claim 3, wherein $R^1$ is hydrogen and $R^2$, is methyl.

5. The compound according to claim 1, wherein Y is selected from the group consisting of halide, —$N_3$, —CN, RO—, $NH_2O$—, NHRO—, $NR_2O$—, $RCO_2$—, $ROCO_2$—, $RNCO_2$—, RS—, RC(S)O—, $RCS_2$—, RSC(0)S—, $RSCS_2$—$RSCO_2$—, ROC(S)O—, $ROCS_2$—, $RSO_2$—, $RSO_3$—, $ROSO_2$—, $ROSO_3$—, $RPO_3$—, $ROPO_3$—, imidazolyl, N-triazolyl, N-benzotriazolyl, benzotriazolyloxy, imidazolyloxy, N-imidazolinone, N-imidazolone, N-imidazolinethione, N-succinimidyl, N-phthalimidyl, N-succinimidyloxy, N-phthalimidyloxy, N-(5-norbornen-2,3-dicarboxyimidyloxy), 2-thioxothiazolidine-3-yl, —ON═(CN)R, 2-pyridyloxy, phenoxy, p-chlorophenoxy, p-nitrophenoxy, trichlorophenoxy, and pentachlorophenoxy, and
wherein R is an alkyl group or an aryl group.

6. The compound according to claim 5, wherein Y is selected from the group consisting of N-succinimidyloxy, 1-benzotriazolyloxy, N-phthalimidyloxy, N-(5-norbornen-2,3-dicarboxyimidyloxy), p-nitrophenoxy, 2-thioxothiazolidine-3-yl, and imidazolyl.

7. The compound according to claim 6, wherein Y is N-succinimidyloxy.

8. The compound according to claim 1, wherein X is selected from the group consisting of O and NH.

9. The compound according to claim 8, wherein X is O.

10. The compound according to claim 1, wherein n is 1.

11. The compound according to claim 1, wherein n is 2.

12. A compound selected from the group consisting of 4-(((2,5-dioxopyrrolidin-l-yloxy)carbonyloxy)methyl)phenyl 4-(2-methoxypolyethoxy)-2-methylbutanoate;
4-(((2,5-dioxopyrrolidin-l-yloxy)carbonyloxy)methyl) phenyl 4-(2-methoxypolyethoxy)-2,2-dimethylbutanoate;
4-(((2,5-dioxopyrrolidin-l-yloxy)carbonyloxy)methyl) phenyl 5-(2-methoxypolyethoxy)-2,2-dimethylpentanoate;
4-(((2,5-dioxopyrrolidin-l-yloxy)carbonyloxy)methyl) phenyl 6-(2-methoxypolyethoxy)-2,2-dimethylhexanoate;
4-(((2,5-dioxopyrrolidin-l-yloxy)carbonyloxy)methyl) phenyl 2-ethyl-5-(2-methoxypolyethoxy)pentanoate;
4-(((2,5-dioxopyrrolidin-l-yloxy)carbonyloxy)methyl) phenyl 5-(2-methoxypolyethoxy)-2-propylpentanoate;
4-(((2,5-dioxopyrrolidin-l-yloxy)carbonyloxy)methyl) phenyl 2-(2-(2-methoxyethoxy)ethyl)hexanoate;
4-(((2,5-dioxopyrrolidin-l-yloxy)carbonyloxy)methyl) phenyl 3-(2-methoxypolyethoxy)-2,2-dimethylpropanoate;
4-(((2,5-dioxopyrrolidin-l-yloxy)carbonyloxy)methyl) phenyl 2(2-methoxypolyethoxy)methyl)-2-methylbutanoate;
4-(((2,5-dioxopyrrolidin-l-yloxy)carbonyloxy)methyl) phenyl 2-ethyl-2-((2-methoxypolyethoxy)methyl)butanoate;
4-(((2,5-dioxopyrrolidin-l-yloxy)carbonyloxy)methyl) phenyl 2(2-methoxypolyethoxy)methyl)-2-methylpentanoate;
4-(((2,5-dioxopyrrolidin-l-yloxy)carbonyloxy)methyl) phenyl 2(2-methoxypolyethoxy)methyl)-2-propylpentanoate;
4-(((2,5-dioxopyrrolidin-l-yloxy)carbonyloxy)methyl) phenyl 2(2-methoxypolyethoxy)methyl)-3-methylbutanoate;
4-(((2,5-dioxopyrrolidin-l-yloxy)carbonyloxy)methyl) phenyl 2(2-methoxypolyethoxy)methyl)hexanoate; and
4-(((2,5-dioxopyrrolidin-l-yloxy)carbonyloxy)methyl) phenyl 3-(2-methoxyethoxy)-2-methylpropanoate.

13. A drug conjugate of Formula II:

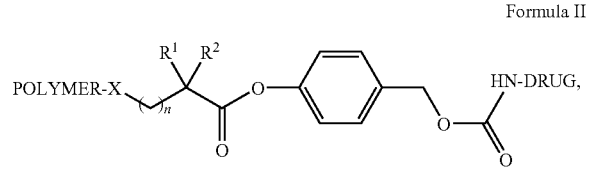

Formula II wherein X is selected from the group consisting of O, S and $NR^3$;
n is 1 or 2;
POLYMER is a water soluble, non-peptidic polymer wherein POLYMER does not comprise a poly(alkylene glycol);
$R^1$, and $R^2$, are independently selected from the group consisting of hydrogen, $(C_1-C_6)$-alkyl, $(C_1-C_6)$-alkylenearyl, and aryl with the proviso that at least one of $R^1$, and $R^2$, is different from hydrogen;

$R^3$, is selected from the group consisting of hydrogen, $(C_1-C_6)$-alkyl, $(C_1-C_6)$-alkylenearyl, and aryl; and DRUG is an amino-containing molecule, peptide, or protein, or a pharmaceutically acceptable salt, ester, or solvate thereof.

14. The drug conjugate according to claim 13, wherein DRUG is a plasma protein or a blood coagulation factor.

15. The drug conjugate according to claim 14, wherein DRUG is selected from the group consisting of erythropoietin, Factor H, Factor VIII, von Willebrand Factor, Factor VIIa, and Factor IX.

16. The drug conjugate according to claim 14, wherein DRUG is Factor VIII.

17. A pharmaceutical formulation comprising the drug conjugate of claim 13 and a pharmaceutically acceptable excipient.

18. The pharmaceutical formulation of claim 17, wherein the formulation is encapsulated in a microparticle.

19. The compound according to claim 1, selected from the group consisting of:

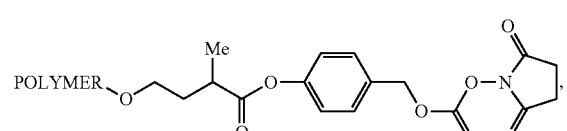

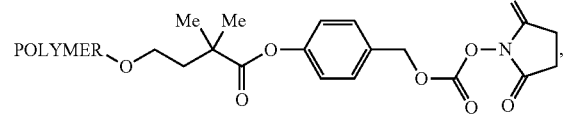

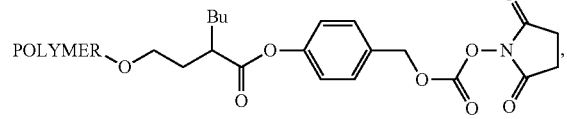

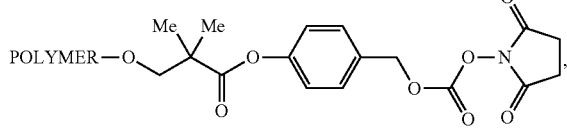

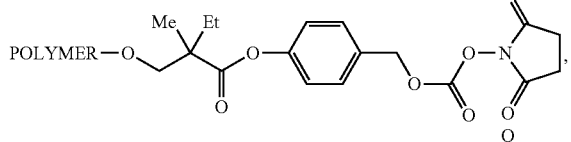

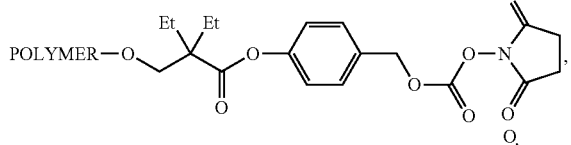

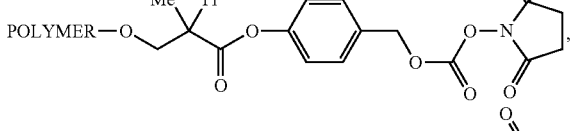

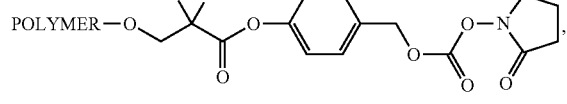

-continued

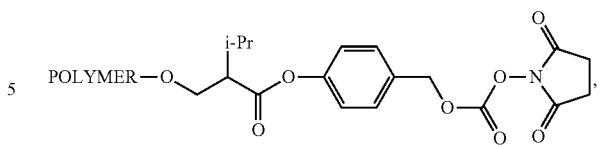

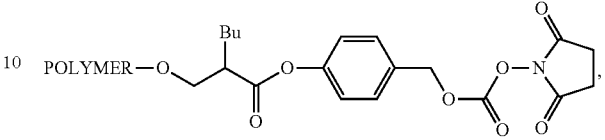

and

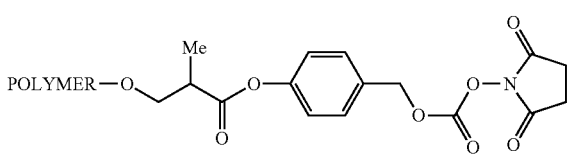

20. The compound according to claim 19, wherein POLYMER is polysialic acid.

21. The compound of claim 20, having a structure

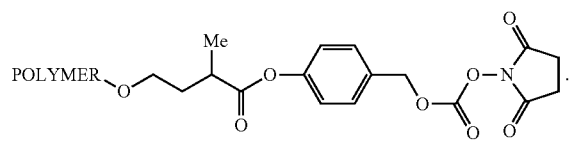

22. The compound of claim 20, having a structure

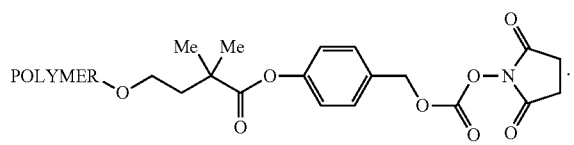

23. The compound of claim 20, having a structure

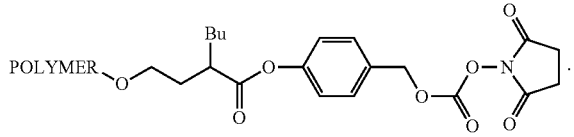

24. The compound of claim 20, having a structure

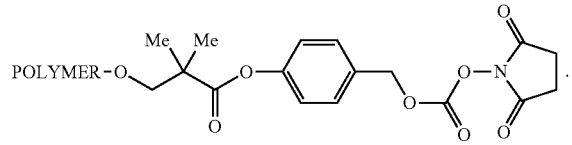

25. The compound of claim 20, having a structure

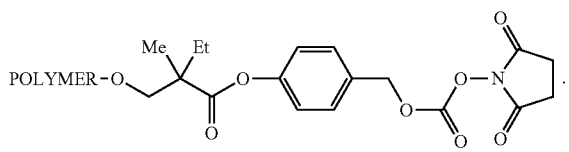

26. The compound of claim 20, having a structure

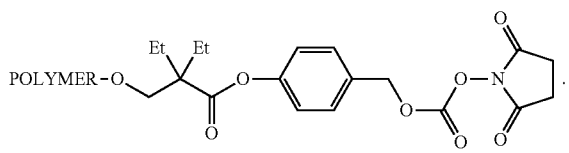

27. The compound of claim 20, having a structure

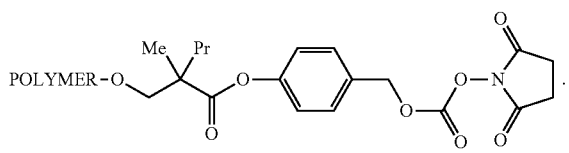

28. The compound of claim 20, having a structure

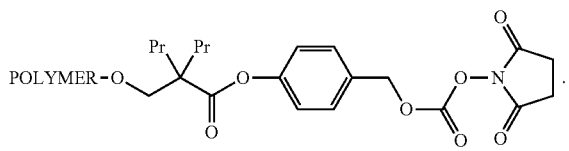

29. The compound of claim 20, having a structure

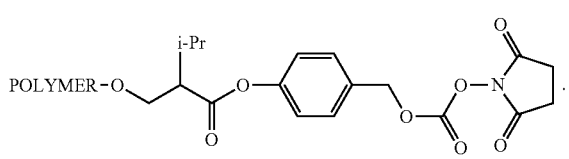

30. The compound of claim 20, having a structure

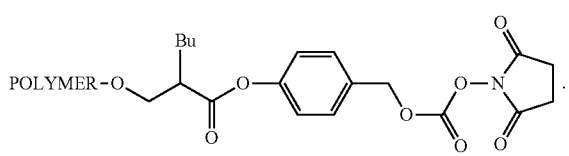

31. The compound of claim 20, having a structure

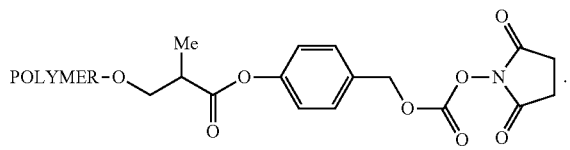

32. A compound having a structure selected from the group consisting of

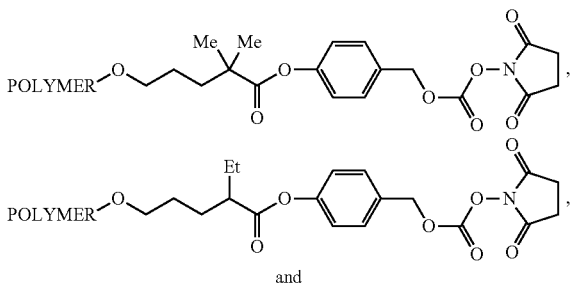

and

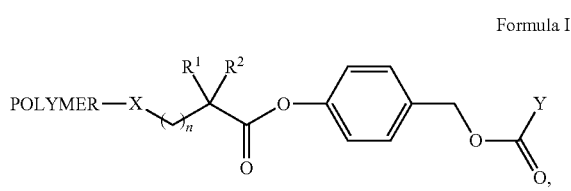

wherein POLYMER is polysialic acid.

33. A compound of Formula I:

Formula I

POLYMER—X—(CR$^1$R$^2$)$_n$—...—Y wherein Y is an activating group;
X is selected from the group consisting of O, S and NR$^3$;
n is 1 or 2;
POLYMER is a water soluble, non-peptidic polymer wherein POLYMER comprises a poly(alkylene glycol);
R$^1$, is hydrogen;
R$^2$, is selected from the group consisting of (C$_1$-C$_6$)-alkyl, (C$_1$-C$_6$)-alkylenearyl, and aryl; and
R$^3$, is selected from the group consisting of hydrogen, (C$_1$-C$_6$)-alkyl, (C$_1$-C$_6$)-alkylenearyl, and aryl.

34. The compound according to claim 33, wherein the poly(alkylene glycol) comprises poly(ethylene glycol) (PEG).

35. The compound according to claim 34, wherein the PEG has a molecular weight of about 200, to about 500,000.

36. The compound according to claim 33, wherein R$^2$, is selected from the group consisting of methyl, ethyl, n-propyl, isopropyl and n-butyl.

37. The compound according to claim 33, wherein Y is selected from the group consisting of N-succinimidyloxy, 1-benzotriazolyloxy, N-phthalimidyloxy, N-(5-norbornen-2,3-dicarboxylmidyloxy), p-nitrophenoxy, 2-thioxothiazolidine-3-yl, and imidazolyl.

38. The compound according to claim 33, selected from the group consisting of:

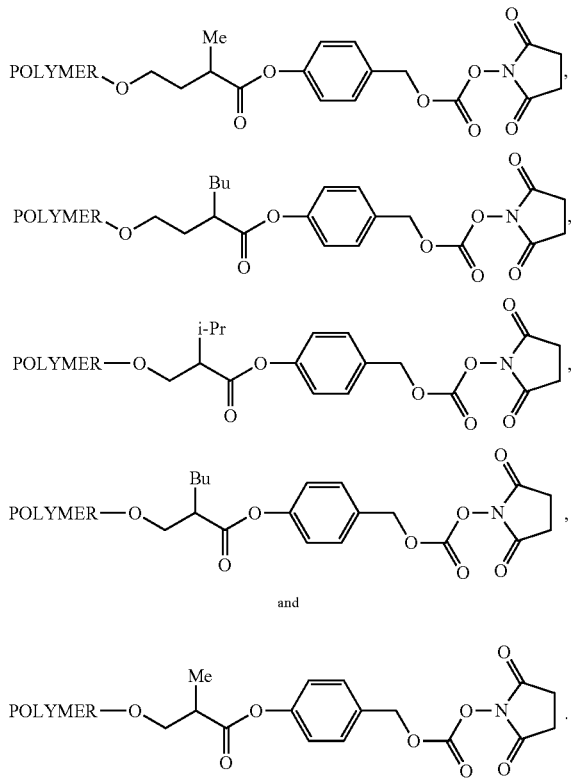

and

39. A drug conjugate of Formula II:

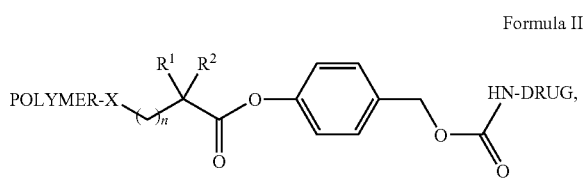

Formula II

X is selected from the group consisting of O, S and $NR^3$;
n is 1 or 2;
POLYMER is a water soluble, non-peptidic polymer wherein POLYMER comprises a poly(alkylene glycol);
$R^1$ is hydrogen;
$R^2$ is selected from the group consisting of $(C_1\text{-}C_6)$-alkyl, $(C_1\text{-}C_6)$-alkylenearyl, and aryl;
$R^3$ is selected from the group consisting of hydrogen, $(C_1\text{-}C_6)$-alkyl, $(C_1\text{-}C_6)$-alkylenearyl, and aryl; and
DRUG is an amino-containing molecule, peptide, or protein, or a pharmaceutically acceptable salt, ester, or solvate thereof.

40. The drug conjugate according to claim 39, wherein DRUG is a plasma protein or a blood coagulation factor.

41. The drug conjugate according to claim 40, wherein DRUG is selected from the group consisting of erythropoietin, Factor H, Factor VIII, von Willebrand Factor, Factor VIIa, and Factor IX.

42. The drug conjugate according to claim 40, wherein DRUG is Factor VIII.

43. A pharmaceutical formulation comprising the drug conjugate of claim 39 and a pharmaceutically acceptable excipient.

44. The pharmaceutical formulation of claim 43, wherein the formulation is encapsulated in a microparticle.

* * * * *

UNITED STATES PATENT AND TRADEMARK OFFICE
CERTIFICATE OF CORRECTION

PATENT NO. : 8,653,131 B2
APPLICATION NO. : 12/545406
DATED : February 18, 2014
INVENTOR(S) : Guohan Yang et al.

Page 1 of 1

It is certified that error appears in the above-identified patent and that said Letters Patent is hereby corrected as shown below:

On the Title Page

At Item (73), Line 3, "Deefield," should be -- Deerfield --.

In the Claims

At Column 43, Line 50, "RSC(0)S--," should be -- RSC(O)S--, --.

At Column 43, Line 51, "RSCS$_2$--RSCO$_2$--," should be -- RSCS$_2$--, RSCO$_2$--, --.

At Column 43, Line 58, "(CN)R," should be -- C(CN)R, --.

Signed and Sealed this
Twenty-first Day of April, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,653,131 B2 | Page 1 of 1 |
| APPLICATION NO. | : 12/545406 | |
| DATED | : February 18, 2014 | |
| INVENTOR(S) | : Guohan Yang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 409 days.

Signed and Sealed this
Twenty-first Day of July, 2015

Michelle K. Lee
*Director of the United States Patent and Trademark Office*